United States Patent
Sakashita et al.

(10) Patent No.: US 9,349,050 B2
(45) Date of Patent: May 24, 2016

(54) MICROSTRUCTURE ANALYSIS METHOD, PROGRAM FOR SAME, AND MICROSTRUCTURE ANALYSIS APPARATUS

(71) Applicant: NGK Insulators, Ltd., Nagoya (JP)

(72) Inventors: Satoshi Sakashita, Yokkaichi (JP); Hiroyuki Nagaoka, Kakamigahara (JP); Ayaka Sakai, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 14/663,524

(22) Filed: Mar. 20, 2015

(65) Prior Publication Data
US 2015/0278602 A1 Oct. 1, 2015

(30) Foreign Application Priority Data
Mar. 31, 2014 (JP) ................................ 2014-072361

(51) Int. Cl.
*G06K 9/00* (2006.01)
*G01B 11/24* (2006.01)
(Continued)

(52) U.S. Cl.
CPC ............ *G06K 9/00624* (2013.01); *G01B 11/24* (2013.01); *G01N 15/082* (2013.01); *G01N 15/088* (2013.01); *G01N 23/046* (2013.01); *G06K 9/52* (2013.01); *G06T 7/0042* (2013.01); *G06T 7/20* (2013.01); *C04B 38/06* (2013.01);
(Continued)

(58) Field of Classification Search
CPC ........................... G01N 15/088; G06T 7/0051
See application file for complete search history.

(56) References Cited

U.S. PATENT DOCUMENTS 5,436,980 A * 7/1995 Weeks .................... B29C 70/28
356/36
5,717,778 A * 2/1998 Chu .................... G01N 21/8483
382/133
(Continued)

FOREIGN PATENT DOCUMENTS

EP 2 669 667 A1 12/2013
EP 2 703 371 A1 3/2014
(Continued)

OTHER PUBLICATIONS

U.S. Appl. No. 14/663,537, filed Mar. 20, 2015, Sakashita, et al.
(Continued)

*Primary Examiner* — Gandhi Thirugnanam
(74) *Attorney, Agent, or Firm* — Burr & Brown, PLLC

(57) ABSTRACT

Plural of virtual curved surface solids, each of which is a curved surface solid formed by a combination of plural of virtual spheres, is placed so as to fill in space voxels, referring to porous-body data in which positional information is associated with voxel-type information (step S100). Information regarding a flow rate for each space voxel when a fluid passes through a porous body is derived by executing a fluid analysis based on the porous-body data (step S110). A flow-rate-weighted mean diameter Ru, which is a weighted average obtained by weighting an equivalent diameter $R'_i$ for each virtual curved surface solid with a volume $V_i$ and an average flow rate $U_i$ for each virtual curved surface solid, is derived based an information regarding the virtual curved surface solids and information regarding the flow rate for each space voxel (step S120).

7 Claims, 11 Drawing Sheets

(51) Int. Cl.
*G06K 9/52* (2006.01)
*G06T 7/20* (2006.01)
*G06T 7/00* (2006.01)
*G01N 15/08* (2006.01)
*G01N 23/04* (2006.01)
*C04B 38/06* (2006.01)
*G01N 33/38* (2006.01)

(52) U.S. Cl.
CPC ........ *G01N 33/388* (2013.01); *G01N 2015/084* (2013.01); *G01N 2015/0846* (2013.01); *G01N 2223/419* (2013.01); *G01N 2223/649* (2013.01); *G06T 7/0051* (2013.01)

(56) References Cited

U.S. PATENT DOCUMENTS

| | | | | |
|---|---|---|---|---|
| 2004/0193035 | A1* | 9/2004 | Gharib | A61B 5/0263 600/407 |
| 2011/0004447 | A1* | 1/2011 | Hurley | G06T 17/00 703/1 |
| 2013/0336578 | A1* | 12/2013 | Sakashita | C04B 38/00 382/154 |
| 2015/0107206 | A1* | 4/2015 | Sakashita | C04B 35/565 55/523 |
| 2015/0278602 | A1* | 10/2015 | Sakashita | G06K 9/00624 382/103 |

FOREIGN PATENT DOCUMENTS

| | | |
|---|---|---|
| JP | 2011-079732 A1 | 4/2011 |
| WO | 2013/146498 A1 | 10/2013 |

OTHER PUBLICATIONS

Hu Dong, et al., "Pore-Network Extraction from Micro-Computerized-Tomography Images," Physical Review E, vol. 80, No. 3, Sep. 2009, pp. 036307-1 to 036307-11.

Extended European Search Report (Application No. 15160213.3) dated Aug. 28, 2015.

* cited by examiner

MICROSTRUCTURE ANALYSIS METHOD, PROGRAM FOR SAME, AND MICROSTRUCTURE ANALYSIS APPARATUS

BACKGROUND OF THE INVENTION

1. Field of the Invention

The present invention relates to a microstructure analysis method, a program for the same, and a microstructure analysis apparatus.

2. Description of the Related Art

As one of methods for analyzing the microstructure of, e.g., pores in a porous body, there is proposed a method of obtaining three-dimensional voxel data of the porous body with a CT scan, and performing an analysis based on the obtained voxel data. For example, Patent Literature (PTL) 1 discloses a pore continuity analysis method of placing virtual spheres having various radia in a way of filling voxels that represent spaces in the voxel data, and deriving continuity of pores from one exposed surface of a porous body to the other exposed surface based on information regarding the placed virtual spheres. PTL 2 discloses a technique of placing a plurality of virtual curved surface solids, which are formed by parent virtual spheres and child virtual spheres, in a way of filling voxels that represent spaces in the voxel data, and analyzing the microstructure of a porous body based on information regarding the placed virtual curved surface solids.

CITATION LIST

Patent Literature

PTL 1: Japanese Unexamined Patent Application Publication No. 2011-079732
PTL 2: International Publication No. 2013/146498

SUMMARY OF THE INVENTION

As disclosed in PTL 1 and 2, by simulating complicatedly-shaped pores in a porous body with virtual spheres, various evaluations can be made on the porous body based an information regarding the virtual spheres. It is demanded to more accurately analyze the microstructure of a porous body by employing the above-mentioned virtual spheres, and to utilize such a technique for evaluating the trapping performance, for example, when the porous body is used as a filter.

The present invention has been accomplished with intent to solve the above-described problems, and an object of the present invention is to more accurately analyze the trapping performance of a porous body.

A microstructure analysis method of the present invention is a method of analyzing a microstructure of a porous body using porous-body data in which positional information indicating position of a voxel obtained by three-dimensionally scanning the porous body is associated with voxel-type information indicating whether the voxel is a space voxel representing space or a matter voxel representing object, the method comprising the steps of:

(a) a step of taking a curved surface solid formed by one virtual sphere or a combination of a plurality of virtual spheres as a virtual curved surface solid, and placing the plurality of virtual curved surface solids so as to fill in the space voxels with curved surface solid voxels which are voxels occupied by the virtual curved surface solid, referring to the porous-body data, (b) a step of deriving information regarding a flow rate for each of the space voxels when a fluid passes through the porous body by executing a fluid analysis based on the porous-body data; and (c) a step of analyzing microstructure of the porous body by deriving, based on information regarding the placed virtual curved surface solids, an equivalent diameter which is a diameter resulting when the virtual curved surface solid is converted to a sphere and a volume of the virtual curved surface solid, for each of the virtual curved surface solids, deriving an average flow rate of the fluid passing through the virtual curved surface solid for each of the virtual curved surface solids based on both the information regarding the placed virtual curved surface solids and the information regarding the flow rate for each of the space voxels, and deriving a flow-rate-weighted mean diameter that is a weighted average obtained by weighting the equivalent diameter for each of the virtual curved surface solids with the volume and the average flow rate for each of the virtual curved surface solids.

According to the microstructure analysis method described above, a plurality of virtual curved surface solids, each of which is given as a curved surface solid formed by one virtual sphere or a combination of a plurality of virtual spheres, is first placed in a way of filling space voxels with curved surface solid voxels, which are occupied by the virtual curved surface solids, by referring to porous-body data that contains positional information and voxel-type information in linked relation. Thus, complicatedly-shaped spaces (pores) inside a porous body are simulated by an assembly of the plurality of virtual curved surface solids. Then, information regarding a flow rate for each space voxel when a fluid passes through the porous body is derived by executing a fluid analysis based on the porous-body data. Furthermore, a flow-rate-weighted mean diameter, which is a weighted average obtained by weighting an equivalent diameter for each virtual curved surface solid with a volume and an average flow rate for each virtual curved surface solid, is derived in accordance with information regarding the virtual curved surface solids and the information regarding the flow rate for each space voxel. In this respect, the inventors have found that trapping performance of the porous body, when used as a filter, is highly correlated to the flow-rate-weighted mean diameter. The reason is presumably as follows. There is a tendency that, as the volumes of and the average flow rates in the plurality of placed virtual curved surface solids vary to a larger extent among the plurality of virtual curved surface solids, the value of the flow-rate-weighted mean diameter tends to be excessively large or small. In a pore of the porous body, the pore being simulated by the virtual curved surface solid having a large volume, there is a tendency that a contact rate of the passing fluid with respect to the wall surface of the porous body reduces. In a pore of the porous body, the pore being simulated by the virtual curved surface solid having a small volume, there is a tendency that the fluid is harder to pass through the pore, and that a catalyst coated over the wall surface of the pore to employ the porous body as a filter is not coated properly. In a pore of the porous body, the pore being simulated by the virtual curved surface solid having the average flow rate higher than an average flow rate (simple average flow rate) for all the pores in the porous body, there is a tendency that the pore is less contributable to the trapping performance because the fluid passes through the pore in a shorter time. In a pore of the porous body, the pore being simulated by the virtual curved surface solid having the average flow rate lower than the average flow rate (simple average flow rate) for all the pores in the porous body, there is a tendency that the pore is less contributable to the trapping performance because the inflow amount of the fluid is small. Thus, the pore of the porous body, which is simulated by the virtual curved surface solid having a too large or small value of the volume or a too high or low value of the average flow rate, tends to be less contributable to the trapping performance. It is hence deemed that, in the porous body in which the pores being less contributable to the trapping performance occupy a large part, the derived value of the flow-rate-weighted mean diameter becomes too large or too small, and that correlation exists between the trapping performance and the flow-rate-weighted mean diameter. Therefore, the trapping performance of the porous body can be analyzed with relatively high accuracy by deriving the flow-rate-weighted mean diameter in the microstructure analysis. Here, the "information regarding the virtual curved surface solids" may be information regarding, e.g., central coordinates and diameters of the virtual spheres constituting the virtual curved surface solids, or positional information of the curved surface solid voxels occupied by the virtual curved surface solids. The "fluid analysis" may be, e.g., an analysis in accordance with the lattice Boltzmann method. Furthermore, the fluid analysis may be performed in connection with the case where the fluid flows into the porous body through a predetermined inflow plane thereof, or the case where the fluid flows from a predetermined inflow plane to a predetermined outflow of the porous body. The "rate for each space voxel" may be a vector quantity or a scalar quantity. When the virtual curved surface solid is constituted by one virtual sphere, a diameter of the one virtual sphere may be used, as it is, as the equivalent diameter. When the virtual curved surface solid is constituted by a combination of plurality of virtual spheres, the equivalent diameter may be derived from a formula of (equivalent diameter=6×volume V of the virtual curved surface solid)/surface area S of the virtual curved surface solid). It is more preferable to place the virtual curved surface solid, which is formed by a combination of plurality of virtual spheres, than placing the virtual curved surface solid that is constituted by one virtual sphere. The reason is that, in the former case, a complicatedly-shaped space (pore) in the porous body can be simulated with higher accuracy and analysis accuracy is increased.

In the microstructure analysis method described above, in the step (c), when the derived flow-rate-weighted mean diameter is in a predetermined range, the trapping performance of the porous body may be determined to be good. The predetermined range may be, for example, not less than 10 μm and not more than 20 μm.

In the microstructure analysis method of the present invention, in the step (c), the flow-rate-weighted mean diameter may be derived from the following formula (1).

[Math. 1]

$$Ru = \frac{\sum_{i=1}^{n} (R'_i \times V_i \times U_i)}{\sum_{i=1}^{n} (V_i \times U_i)} \quad \text{formula (1)}$$

Where,
Ru: flow-rate-weighted mean diameter
n: number of virtual curved surface solids that have been placed
$R'_i$: equivalent diameter of each virtual curved surface solid (i=1, 2, ..., n)
$V_i$: volume of each virtual curved surface solid (i=1, 2, ..., n)
$U_i$: average flow rate of fluid passing through each virtual curved surface solid (i=1, 2, ..., n).

In the microstructure analysis method described above, in the step (c), the microstructure of the porous body may be analyzed by deriving an average value of the equivalent diameters of the plurality of virtual curved surface solids or obtaining an average pore diameter of the porous body to be set as an arithmetic mean diameter, and by deriving a difference between the arithmetic mean diameter and the flow-rate-weighted mean diameter. Here, when the flow-rate-weighted mean diameter takes a comparable value, the trapping performance of the porous body tends to be higher as an absolute value of the difference between the arithmetic mean diameter and the flow-rate-weighted mean diameter reduces. Accordingly, the trapping performance of the porous body can be analyzed with higher accuracy by deriving the difference between the arithmetic mean diameter and the flow-rate-weighted mean diameter in the microstructure analysis. In this respect, in the step (c), the trapping performance of the porous body may be determined to be better on condition that, when the derived flow-rate-weighted mean diameter is in the predetermined range and when the trapping performance of the porous body is determined to be good, the derived absolute value of the difference between the arithmetic mean diameter and the flow-rate-weighted mean diameter is in a predetermined range. The predetermined range of the absolute value may be set to 2 μm or less, for example.

In the microstructure analysis method of the present invention, in the step (a), a curved surface solid including a parent virtual sphere and one or more child virtual spheres with which voxels occupied by the parent virtual sphere partially overlap is taken as the virtual curved surface solid, and the plurality of virtual curved surface solids may be placed.

In the microstructure analysis method of the present invention, in the step (a), the virtual curved surface solid having the larger equivalent diameter may be preferentially placed. This enables the space voxels to be filled with the virtual curved surface solids having volumes as large as possible.

In the microstructure analysis method of the present invention, in the step (a), the plurality of virtual curved surface solids may be placed by executing processing on the porous-body data through the steps of placing one parent virtual sphere with a maximum diameter among the parent virtual spheres, which can be placed in a way of not overlapping with any matter voxel and filling the space voxels, placing one or more child virtual spheres such that a center of each child virtual sphere overlaps with the parent virtual sphere, and that voxels occupied by each child virtual sphere do not overlap with the matter voxel and fill the space voxels, placing one virtual curved surface solid, which is formed by the parent virtual sphere and the one or more child virtual spheres, in a way of filling the space voxels with the curved surface solid voxels that are voxels occupied by the virtual curved surface solid, and repeating the aforementioned steps. With the above-described method, since the virtual curved surface solid is placed such that the curved surface solid voxels do not overlap with any matter voxel, a processing time necessary for placing the virtual curved surface solids can be shortened in comparison with the case of allowing the overlapping between the curved surface solid voxels and the matter voxels. Furthermore, since the parent virtual sphere with the maximum diameter among the parent virtual spheres, which can be placed on the above-mentioned condition, is placed, the space voxels can be filled with the virtual curved surface solids having the volumes as large as possible. In this respect, when repeating the process of placing one virtual curved surface solid, the voxels occupied by different virtual curved surface solids are preferably allowed to be overlapped with each other. Alternatively, when repeating the process of placing one virtual curved surface solid, the voxels occupied by different virtual curved surface solids may be selected to be not overlapped with each other.

A program of the present invention causes one or multiple computers to implement each of the steps of the microstructure analysis method of the present invention according to any one of the above-mentioned aspects. The program may be recorded on a computer-readable recording medium (e.g., a hard disk, ROM, FD, CD or DVD), or may be distributed from one computer to another via a transmission medium (communication network such as the Internet or LAN), or may be sent and received in any one of other suitable fashions. By causing one computer to execute the program or by causing multiple computers to execute the steps in a shared manner, the steps of the above-described microstructure analysis method are implemented, and hence similar advantageous effects to those of the above-described microstructure analysis method are obtained.

A microstructure analysis apparatus of the present invention comprises, storage device that stores porous-body data in which positional information indicating position of a voxel obtained by three-dimensionally scanning the porous body is associated with voxel-type information indicating whether the voxel is a space voxel representing space or a matter voxel representing object, virtual curved surface solid placement device that takes a curved surface solid formed by one virtual sphere or a combination of a plurality of virtual spheres as a virtual curved surface solid, and places the plurality of virtual curved surface solids so as to fill in the space voxels with curved surface solid voxels which are voxels occupied by the virtual curved surface solid, referring to the porous-body data, fluid analysis device that derives information regarding a flow rate for each of the space voxels when a fluid passes through the porous body by executing a fluid analysis based on the porous-body data, and microstructure analysis device that analyzes microstructure of the porous body by deriving, based on information regarding the placed virtual curved surface solids, an equivalent diameter which is a diameter resulting when the virtual curved surface solid is converted to a sphere and a volume of the virtual curved surface solid, for each of the virtual curved surface solids, deriving an average flow rate of the fluid passing through the virtual curved surface solid for each of the virtual curved surface solids based on both the information regarding the placed virtual curved surface solids and the information regarding the flow rate for each of the space voxels, and deriving a flow-rate-weighted mean diameter that is a weighted average obtained by weighting the equivalent diameter for each of the virtual curved surface solids with the volume and the average flow rate for each of the virtual curved surface solids.

According to the microstructure analysis apparatus described above, a plurality of virtual curved surface solids, each of which is given as a curved surface solid formed by one virtual sphere or a combination of plurality of virtual spheres, is placed in a way of filling space voxels with curved surface solid voxels, which are occupied by the virtual curved surface solids, by referring to porous-body data that contains positional information and voxel-type information in linked relation. Thus, complicatedly-shaped spaces (pores) in a porous body are simulated by an assembly of the plurality of virtual curved surface solids. Then, information regarding a flow rate for each space voxel when a fluid passes through the porous body is derived by executing a fluid analysis based on the porous-body data. Furthermore, a flow-rate-weighted mean diameter, which is a weighted average obtained by weighting an equivalent diameter for each virtual curved surface solid with a volume and an average flow rate for each virtual curved surface solid, is derived in accordance with information regarding the virtual curved surface solids and the information regarding the flow rate for each space voxel. By deriving the flow-rate-weighted mean diameter as described above, the trapping performance of the porous body can be analyzed with relatively high accuracy. The microstructure analysis apparatus of the present invention may additionally operate the above-described device to perform other operations than those described above, and/or may additionally include other device than those described above in order to implement the steps of the microstructure analysis method according to any one of the above-mentioned aspects.

DETAILED DESCRIPTION OF THE INVENTION

An embodiment of the present invention will be described below with reference to the drawings.

Figure 1:
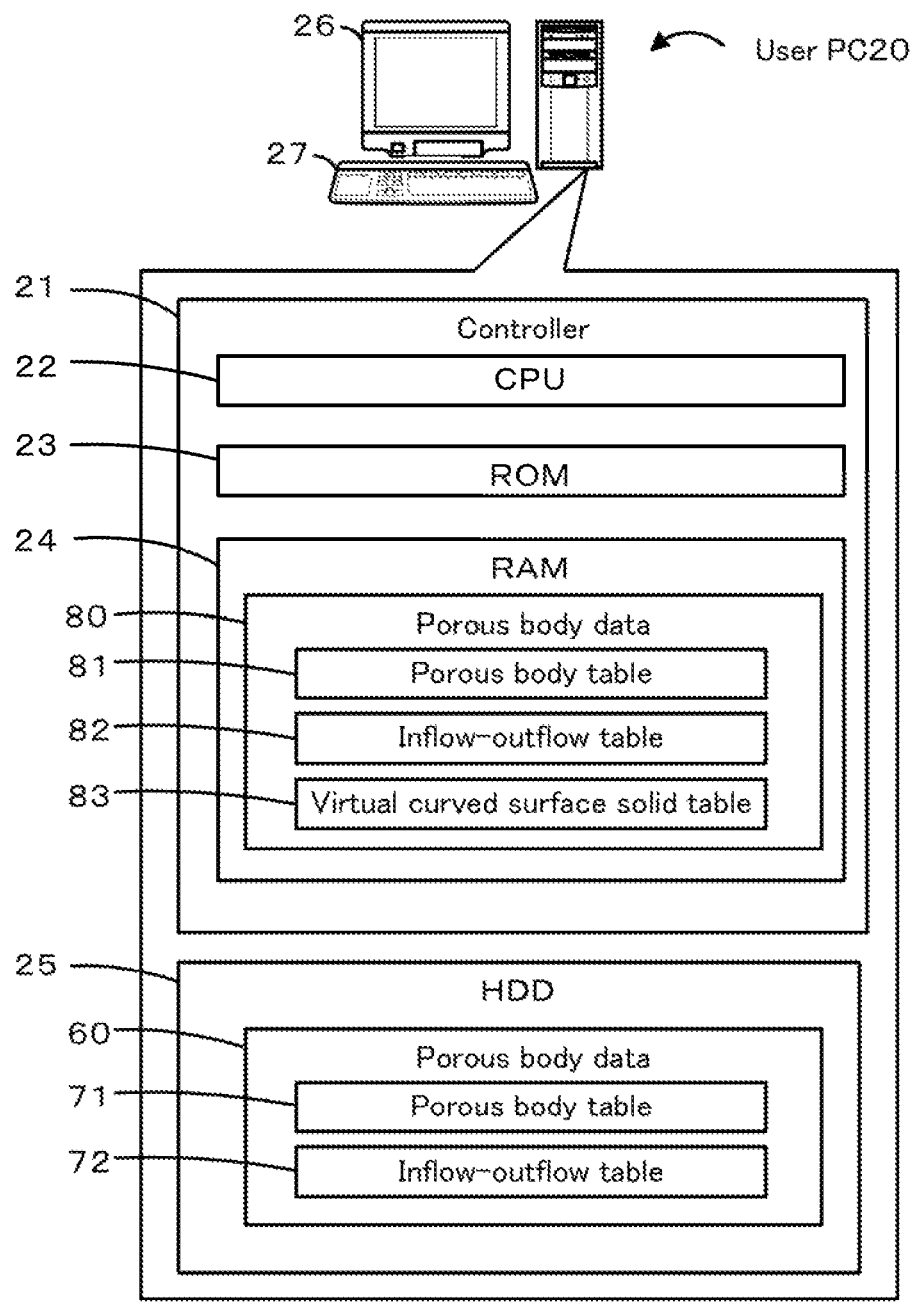
FIG. 1 is a configuration diagram of a user's personal computer 20 embodying the present invention.

FIG. 1 is a configuration diagram of a user's personal computer (PC) 20 embodying one example a microstructure analysis apparatus according to the present invention. The user's PC 20 includes a controller 21 including a CPU 22 that executes various types of processing, a ROM 23 that stores various processing programs, a RAM 24 that temporarily stores data, and so on. The user's PC 20 further includes a HDD 25, i.e., a large-capacity memory, which stores various processing programs such as an analysis processing program, and various data such as porous-body data 60, i.e., three-dimensional voxel data of a porous body. In addition, the user's PC 20 includes a display 26 that displays various kinds of information on a screen, and an input device 27, e.g., a keyboard through which a user inputs various commands. The porous-body data 60 stored in the HDD 25 contains a porous body table 71 and an inflow-outflow table 72, which are described in detail later. The user's PC 20 can analyze the microstructure of the porous body based on the porous-body data 60 stored in the HDD 25. Furthermore, porous-body data 80 is stored in the RAM 24 during the process of analyzing the microstructure. The porous-body data 80 contains a porous body table 81, an inflow-outflow table 82, and a virtual curved surface solid table 83, which are described in detail later.

Figure 2:
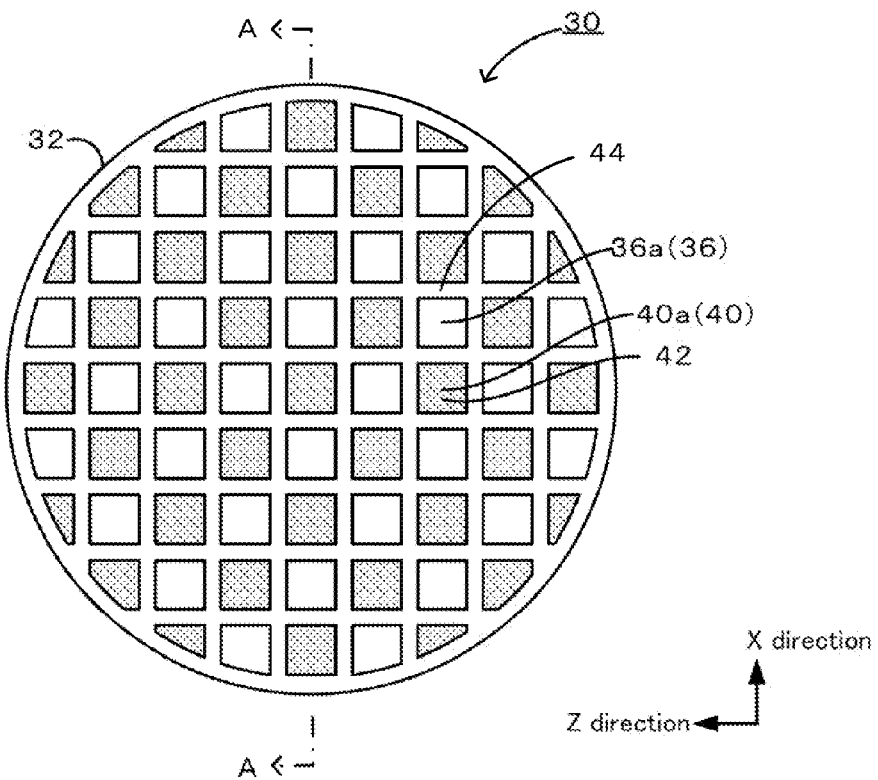
FIG. 2 is a front view of a honeycomb filter 30 including porous partition walls 44.
Figure 3:
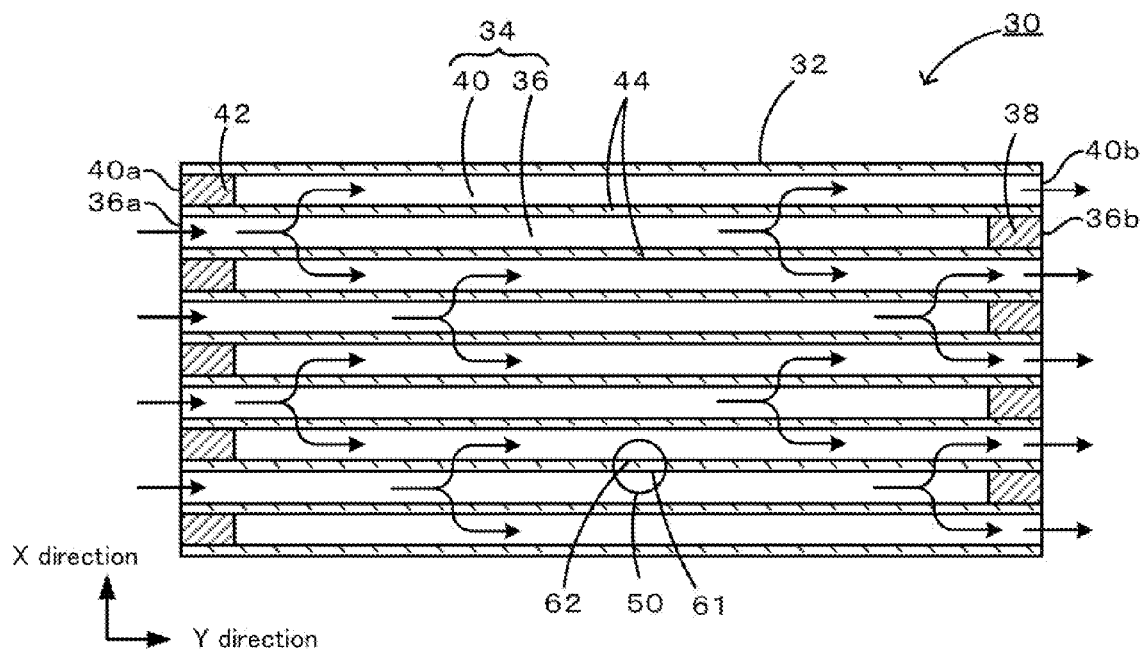
FIG. 3 is a sectional view taken along A-A in FIG. 2.

A porous body to be analyzed by the user's PC 20 is now described. FIG. 2 is a front view of a honeycomb filter 30, i.e., a porous body, including porous partition walls 44, and FIG. 3 is a sectional view taken along A-A in FIG. 2.

The honeycomb filter 30 is a diesel particulate filter (DPF) with the function of filtering particulate matters (PM) in exhaust gas from a diesel engine. The honeycomb filter 30 has many cells 34 (see FIG. 3) partitioned by the porous partition walls 44, and an outer peripheral protective portion 32 formed along an outer periphery of the honeycomb filter 30. The porous partition walls 44 are preferably made of a ceramic material in the form of inorganic particles, e.g., particles of Si-bonded SiC or cordierite, from the viewpoint of strength and heat resistance. The thickness of the porous partition walls 44 is preferably not less than 200 µm and less than 600 µm, and it is 300 µm in this embodiment. The porous partition walls 44 have an average pore diameter (measured by the mercury press-in method) of not less than 10 µm and less than 60 µm, for example, and a porosity (void ratio) of not less than 40% and less than 65%. The many cells 34 formed in the honeycomb filter 30 are grouped, as illustrated in FIG. 3, into inlet opened cells 36 each having an opened inlet 36a and an outlet 36b closed by an outlet closing material 38, and outlet opened cells 40 each having an inlet 40a closed by an inlet closing material 42 and an opened outlet 40b. The inlet opened cells 36 and the outlet opened cells 40 are alternately formed and positioned adjacent to each other. A cell density is not less than 15 cells/an and less than 65 cells/cm$^2$, for example. The outer peripheral protective portion 32 is a layer for protecting the outer periphery of the honeycomb filter 30, and it may contain the above-mentioned inorganic particles, inorganic fibers such as aluminosilicate, alumina, silica, zirconia, ceria, and mullite, binders such as colloidal silica and clay, etc.

The honeycomb filter 30 is mounted downstream of a not-illustrated diesel engine, for example, and is used to purify exhaust gas containing PM before being released to the atmosphere. Arrows in FIG. 3 denote flows of the exhaust gas in such a case. After flowing into the inlet opened cells 36 from the inlets 36a of the honeycomb filter 30, the PM-containing exhaust gas from the diesel engine passes through the porous partition walls 44 to flow into the outlet opened cells 40 adjacent to the inlet opened cells 36, and is then released to the atmosphere from the outlets 40b of the outlet opened cells 40. When the PM-containing exhaust gas passing through the porous partition walls 44 and flows into the outlet opened cells 40 from the inlet opened cells 36, the PM in the exhaust gas is trapped. Therefore, the exhaust gas flowing into the outlet opened cells 40 is clean exhaust gas containing no PM. A not-illustrated oxidation catalyst, e.g., platinum, is coated over inner surfaces of pores within the porous partition walls 44 to oxidize the trapped PM, thereby preventing a reduction of the porosity of the porous partition walls 44 and an abrupt rise of pressure loss.

The honeycomb filter 30 can be manufactured by employing, as a raw material, green body or slurry, which is prepared by mixing a base material, a pore-forming material, and a dispersant, for example. The base material may be the above-mentioned ceramic material. When the base material is SiC, for example, a mixture of SiC powder and metallic Si power at a mass ratio of 80:20 can be used. The pore-forming material is preferably a material that is burnt away when fired later. For example, starch, coke, or foamed resin can be used as the pore-forming material. The dispersant may be a surfactant, such as ethylene glycol. Device for preparing the green body is not limited to particular one, and the green body can be prepared by a method using a kneader, a vacuum earth kneader, for example. The honeycomb filter 30 including the porous partition walls 44 can be manufactured, for example, by extrusion-molding the green body into the shape illustrated in FIGS. 2 and 3 with the use of a mold in the form corresponding to an array of the cells 34, sealing the cells 34 in an obtained molding with the outlet closing material 38 and the inlet closing material 42, and then carrying out drying, calcining and firing processes successively. The outlet closing material 38 and the inlet closing material 42 may be the same as the raw material used to form the porous partition walls 44. The calcining process is a process of removing organic components contained in the honeycomb filter 30 by burning it at temperature lower than a firing temperature. The firing temperature can be set to be 1400° C. to 1450° C. when the raw material is cordierite, and 1450° C. when it is Si-bonded SiC. The honeycomb filter 30 including the porous partition walls 44 can be obtained through the above-described processes.

Three-dimensional voxel data of the porous partition walls 44, which has been obtained by performing a CT scan on the honeycomb filter 30, is stored, as the porous-body data 60, in the HD 25 of the user's PC 20. In this embodiment, the voxel data is obtained by performing the CT scan on condition of setting, as an image capturing section, an XY-plane defined by an X-direction and a Y-direction illustrated in FIG. 3, and capturing images of plurality of image capturing sections along a Z-direction illustrated in FIG. 2. In this embodiment, resolution in each of the X-, Y- and Z-directions is 1.2 µm, and a cube having each side of 1.2 µm, resulting from such setting of the resolution, is a minimum unit, i.e., a voxel, of the three-dimensional voxel data. The resolution in each of the X-, Y- and Z-directions can be set as appropriate depending on the performance of a CT apparatus, the sizes of particles to be analyzed, and so on. The resolutions in the X-, Y- and Z-directions may be set to different values. The resolution in each of the X-, Y- and Z-directions may be set to a value in the range of 0.5 µm to 3.0 µm, for example, though not particularly limited to that range. As the resolution is set to a higher value (namely, as the length of the voxel in each of the X-, Y- and Z-directions is reduced), analysis accuracy is increased. From the viewpoint of analysis accuracy, the resolution in each of the X-, Y- and Z-directions is preferably set to be not more than 3.0 µm. Although an analysis time (calculation time) is prolonged as the resolution is set to a higher value, the resolution in each of the X-, Y- and Z-directions may be set to be less than 0.5 µm. In practice, the resolution may be set to the range of 0.2 µm to 0.3 µm, or less than 0.2 µm, for example. Each voxel is stored in the HDD 25 together with not only its position expressed by XYZ-coordinates (where a coordinate value 1 corresponds to 1.2 µm, i.e., the length of one side of the voxel), but also with type information indicating whether the relevant voxel represents a space (pore) or a matter (constituent material of the porous partition wall 44). In this embodiment, a value 0 is added as the type information to a voxel representing the space (i.e., a space voxel), and a value 9 is added as the type information to a voxel representing the matter (i.e., a matter voxel). In fact, data obtained with the CT scan is, e.g., luminance data for each set of the XYZ-coordinates. The porous-body data 60 used in this embodiment can be obtained by binarizing the luminance data with a specific threshold, and determining whether the voxel is the space voxel or the matter voxel for each set of the coordinates. The specific threshold is predetermined as a value allowing the space voxel and the matter voxel to be discriminated properly. The threshold may be previously set through experiments, for example, such that the measured porosity of the porous partition walls 44 and the porosity in the voxel data after the binarization are substantially equal to each other. The above-described CT scan can be performed, for example, by employing SMX-160CT-SV3 made by Shimadzu Cooperation.

Figure 4A:
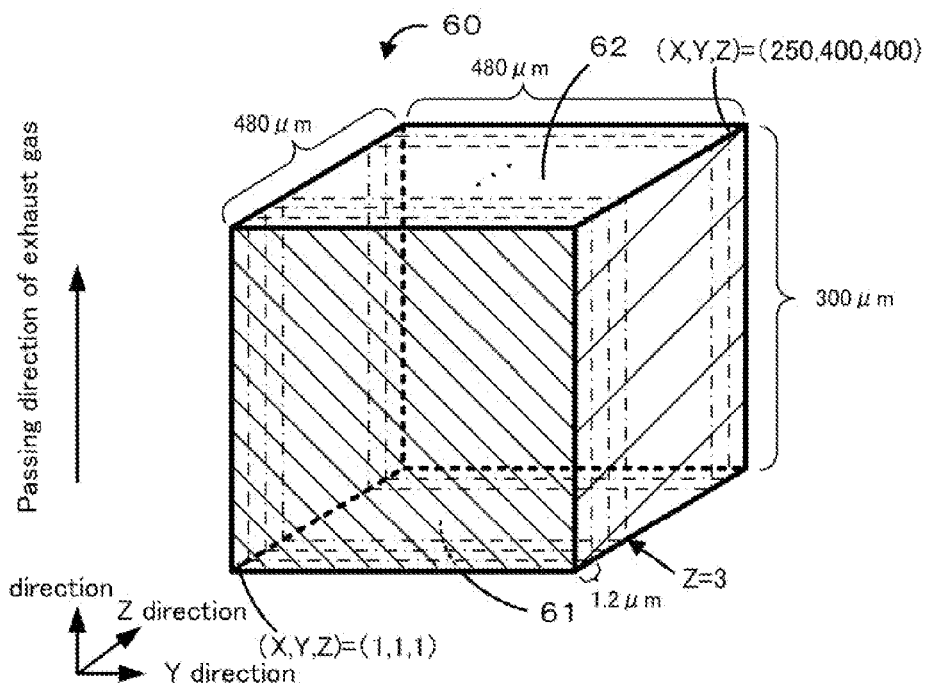
FIG. 4A and FIG. 4B are conceptual views of porous-body data 60.
Figure 4B:
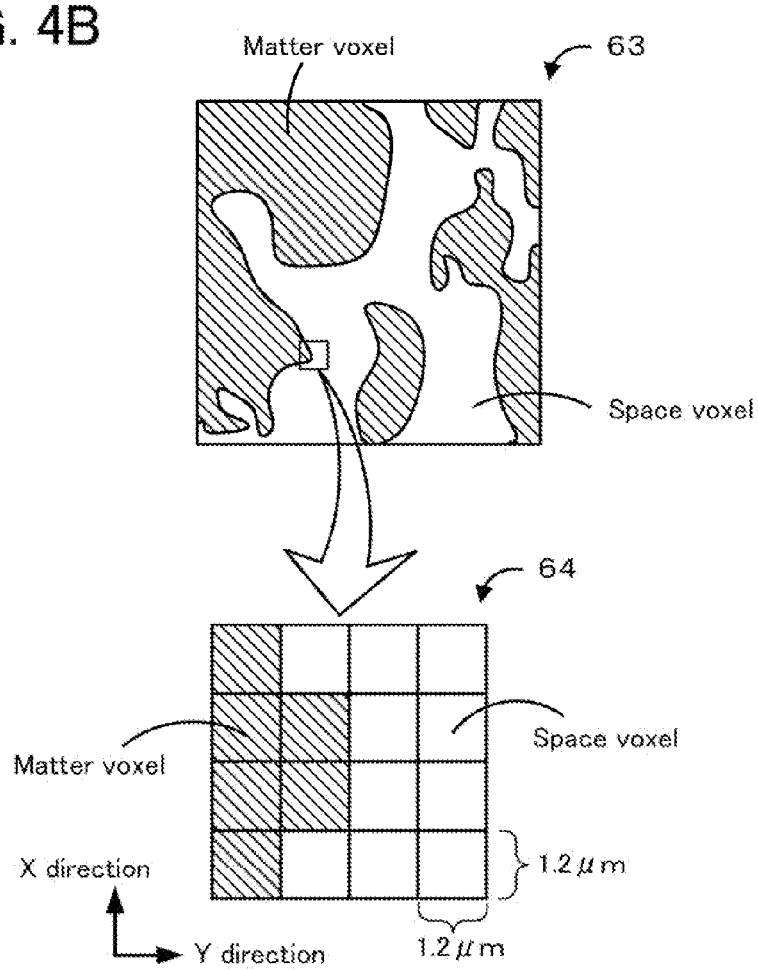
Figure 5:
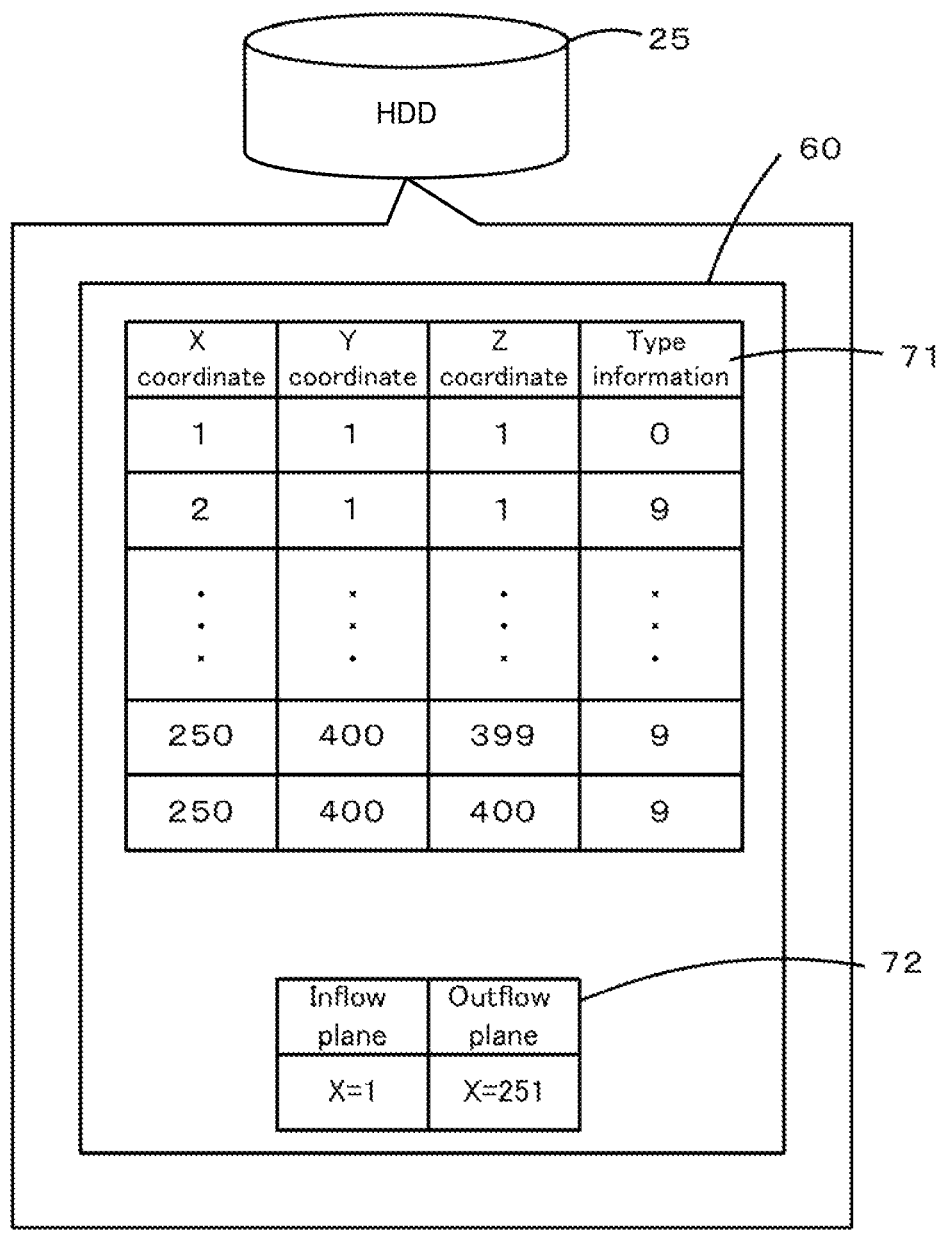
FIG. 5 is an illustration to explain the porous-body data 60.

FIG. 4A and FIG. 4B are conceptual views of the porous-body data 60. FIG. 4A is a conceptual view of the porous-body data 60 that is obtained, as voxel data, by CT-scanning the porous partition wall 44 in a region 50 in FIG. 3. In this embodiment, the porous-body data 60 is obtained by extracting, from the voxel data of the porous partition wall 44, voxel data in a rectangular parallelepiped portion with dimensions of 300 μm (=1.2 μm×250 voxels) in the X-direction, which is the sane value as the thickness of the porous partition wall 44 in a passing direction of the exhaust gas, 480 μm (=1.2 μm×400 voxels) in the Y-direction, and 480 μm (=1.2 m×400 voxels) in the Z-direction. The later-described analysis process is carried out on the porous-body data 60. The size of the porous-body data 60 can be set as appropriate depending on the thickness or size of the porous partition wall 44, the allowable calculation load, and so on. For example, the length in the X-direction is not limited to 300 μm, and it may be a different value insofar as such a value is the same as the thickness of the porous partition wall 44 in the passing direction of the exhaust gas. Although the length in the X-direction is preferably the same value as the thickness of the porous partition wall 44 in the passing direction of the exhaust gas, it is not necessarily to be the same value. Similarly, the lengths in the Y- and Z-directions are not limited to 480 μm, and they may be different from each other between the Y- and Z-directions. In the porous-body data 60, two of six surfaces of the rectangular parallelepiped (i.e., planes parallel to a Y-Z plane) serve as an inflow plane 61 (see FIG. 3), which is a boundary surface between the porous partition wall 44 and the inlet opened cell 36, and as an outflow plane 62 (see FIG. 3), which is a boundary surface between the porous partition wall 44 and the outlet opened cell 40, as denoted in the region 50. The remaining four surfaces are sectional surfaces of the porous partition wall 44. FIG. 4B illustrates an XY-plane (image capturing section) 63 in the porous-body data 60 at a position where a Z-coordinate value is 3, and an enlarged view 64 of a part of the XY-plane 63. As seen from the enlarged view 64, the XY-plane 63 is constituted by an array of voxels each having one side of 1.2 μm, and each voxel is represented by the space voxel or the matter voxel. While the image capturing section obtained with the CT scan is given as planar data having no thickness in the Z-direction as illustrated in FIG. 4B, each image capturing section is handled as having a thickness corresponding to an interval (1.2 μm) between the image capturing sections in the Z-direction. Namely, each voxel is handled as being the rectangular parallelepiped with each side of 1.2 μm, as described above. As illustrated in FIG. 5, the porous-body data 60 is stored in the HDD 25 as data containing the porous body table 71 that represents the XYZ-coordinates, i.e., positional information, and the type information per voxel in linked relation, and the inflow-outflow table 72 representing the inflow plane 61 and the outflow plane 62. "X=1" in the inflow-outflow table 72 illustrated in FIG. 5 indicates a plane at X=1 in the XYZ-coordinate system, and represents the inflow plane 61 as illustrated in FIG. 4A. Similarly, "X=251" represents the outflow plane 62. The HD 25 further stores not only the porous-body data 60, but also other plurality of sets of porous-body data corresponding to voxel data of the porous partition walls 44 other than the above-mentioned region 50.

Figure 6:
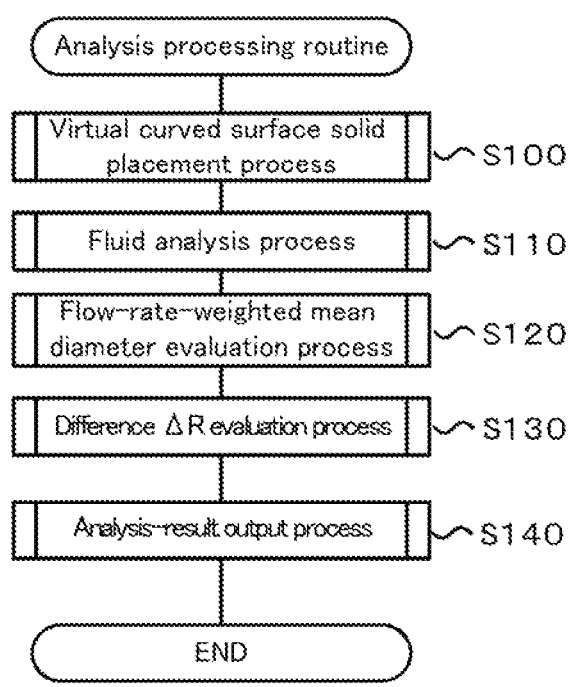
FIG. 6 is a flowchart illustrating one example of an analysis processing routine.

The analysis process executed on the porous-body data 60 by the user's PC 20 will be described below. FIG. 6 is a flowchart of an analysis processing routine. The analysis processing routine is performed by the CPU 22 that executes an analysis processing program stored in the HDD 25 when the user instructs the execution of the analysis process through the input device 27. While the following description is made in connection with the case of executing the analysis process of the porous-body data 60, the analysis process can be similarly executed for the other porous-body data. Which porous-body data is to be analyzed may be set in advance or may be designated by the user.

Upon start of the analysis processing routine, the CPU 22 first executes a virtual curved surface solid placement process, i.e., a process of placing virtual curved surface solids in a way of filling the space voxels in the porous-body data 60 (step S100).

Figure 7:
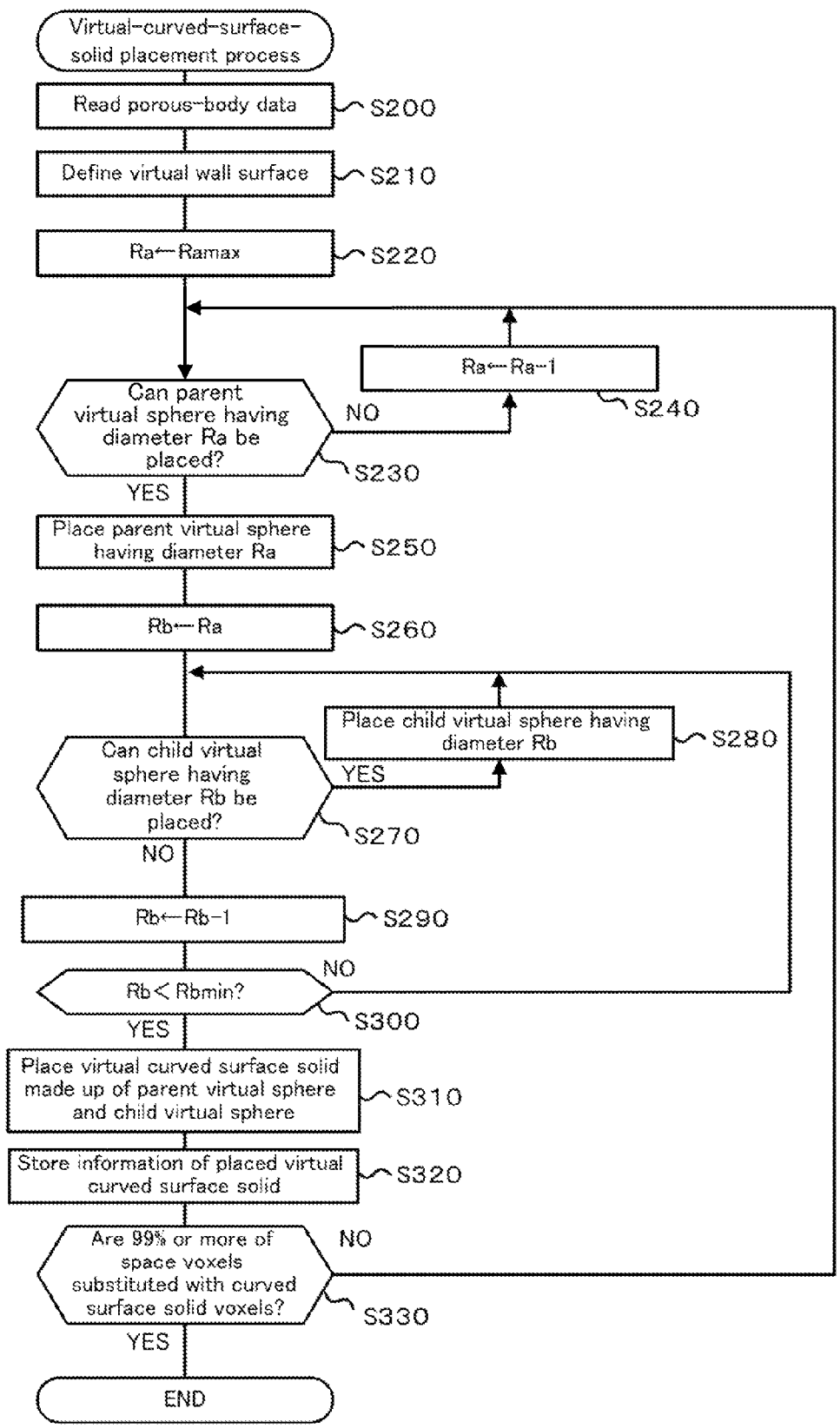
FIG. 7 is a flowchart illustrating one example of a virtual curved surface solid placement process.

The virtual curved surface solid placement process is described here apart from the description of the analysis processing routine. FIG. 7 is a flowchart of the virtual curved surface solid placement process. The virtual curved surface solid placement process is executed by the CPU 22. Upon start of the virtual curved surface solid placement process, the CPU 22 first reads out the porous-body data 60 stored in the Ht 25 and stores the porous-body data 60 in the RAM 24 (step S200). With the step S200, the same data as the porous-body data 60 stored in the RD 25, including the porous body table 71 and the inflow-outflow table 72, is stored in the RAM 24 as the porous-body data 80 including the porous body table 81 and the inflow-outflow table 82. Then, virtual wall surfaces are set for the read-out porous-body data 80 (step S210). More specifically, the user designates, through the input device 27, a distance from the porous-body data 80, which corresponds to the rectangular parallelepiped of 300 μm×480 μm×480 μm, to the virtual wall surfaces surrounding the rectangular parallelepiped. The CPU 22 accepts the designated distance and stores it in the RAM 24. When the distance to the virtual wall surfaces is set to 1 μm, for example, the CPU 22 assumes that the virtual wall surfaces are present at positions away 1 μm outward from the surfaces of the porous-body data 80 in the X-, Y- and Z-directions, and that the outer side of the virtual wall surfaces is entirely filled with the matter voxels. Thus, because the porous-body data 80 corresponds to the rectangular parallelepiped of 300 μm×480 μm×480 μm, the porous-body data 80 is regarded as being covered with the virtual wall surfaces defining a rectangular parallelepiped of 302 μm×482 μm×482 μm. The virtual wall surfaces are set to limit a region where the later-described virtual curved surface solids (parent virtual sphere and child virtual sphere) can be placed.

Then, the CPU 22 sets a diameter Ra of the parent virtual sphere to a maximum value Ramax (step S220), and determines (step S230) whether the parent virtual sphere having the diameter Ra can be placed in the space voxels that are present inside the virtual wall surfaces set in the step S210. The parent virtual sphere having the diameter Ra implies a virtual sphere of which diameter has a value of Ra (μm), and of which center is positioned at a center of any voxel. The determination as to whether the parent virtual sphere having the diameter Ra can be placed is made, for example, as follows. First, one of the space voxels (i.e., the voxels assigned with the type information of the value 0) at that time is selected. If the parent virtual sphere overlaps with the matter voxel when the parent virtual sphere having the diameter Ra is placed with the selected voxel being at the center, another space voxel is selected as another center for the placement. If the parent virtual sphere does not overlap with the matter voxel after successively selecting the space voxels, it is determined that the parent virtual sphere having the diameter Ra can be placed at a position of the relevant space voxel. If the parent virtual sphere overlaps with the matter voxel even after selecting, as the center for the placement, all of the space voxels at that time, it is determined that the parent virtual sphere having the diameter Ra cannot be placed. The voxel providing the center for the placement may be selected at random or in order from the voxel on the inflow plane 61 toward the voxel on the outflow plane 62. The maximum value Ramax may be a value not less than a maximum value among diameters of pores that are usually present in the porous partition wall 44. For example, the maximum value Ramax can be set to a value in consideration of numerical values measured by experiments. If the step S230 determines that the parent virtual sphere cannot be placed, the CPU 22 decrements the value of the diameter Ra by one (step S240), and then executes the processing subsequent to the step S230. While the decremented value is set to one in this embodiment, it can be set as appropriate depending on the allowable calculation load and so on.

If the step S230 determines that the parent virtual sphere can be placed, one parent virtual sphere having the diameter Ra is placed at the relevant position (step S250). More specifically, the type information corresponding to each of the voxels, which are occupied by the parent virtual sphere when the parent virtual sphere having the diameter Ra is placed, those voxels being contained in the porous body table 81 of the porous-body data 80 stored in the RAM 24 in the step S200, is updated to a value 3 indicating that the relevant voxel is occupied by the parent virtual sphere. In this embodiment, when a center of the voxel is included in the parent virtual sphere, the type information of the relevant voxel is updated to the value 3. However, when a volume of the voxel is included in the parent virtual sphere at a specific rate (e.g., 50%) or more, the type information of the relevant voxel may be updated to the value 3. Alternatively, the type information of only the voxel that is completely included in the parent virtual sphere may be updated to the value 3. When even a part of the voxel is occupied by the parent virtual sphere, the type information of the relevant voxel may be updated to the value 3. The above-mentioned point is similarly applied to the voxel occupied by the child virtual sphere described later.

Then, the CPU 22 sets a diameter Rb of the child virtual sphere to the same value as the diameter Ra (step S260), and determines (step S270) whether the child virtual sphere having the diameter Rb can be placed in the space voxels that are present inside the virtual wall surfaces set in the step S210. The child virtual sphere having the diameter Rb implies a virtual sphere of which diameter has a value of Rb ($\mu$m), of which center is positioned at a center of any voxel, and which occupies voxels in partly overlapping relation to the voxels occupied by the parent virtual sphere. The child virtual sphere is placed such that a center of the child virtual sphere overlaps the parent virtual sphere placed in the step S250. The determination as to whether the child virtual sphere having the diameter Rb can be placed is made, for example, as follows. First, one of the voxels occupied by the parent virtual sphere (i.e., the voxels assigned with the type information of the value 3) at that time is selected. If the child virtual sphere overlaps with the matter voxel when the child virtual sphere having the diameter Rb is placed with the selected voxel being the center, another space voxel occupied by the parent virtual sphere is selected as another center for the placement. If the child virtual sphere does not overlap with the matter voxel after successively selecting the space voxels, it is determined that the child virtual sphere having the diameter Rb can be placed at a position of the relevant space voxel. If the child virtual sphere overlaps with the matter voxel even after selecting, as the center for the placement, all of the space voxels occupied by the parent virtual sphere at that time, it is determined that the child virtual sphere having the diameter Rb cannot be placed.

If the step S270 determines that the child virtual sphere can be placed, one child virtual sphere having the diameter Rb is placed at the relevant position (step S280). More specifically, the type information corresponding to each of the voxels, which are occupied by the child virtual sphere when the child virtual sphere having the diameter Rb is placed, those voxels being contained in the porous body table 81 of the porous-body data 80 stored in the RAM 24 in the step S200, is updated to a value 4 indicating that the relevant voxel is occupied by the child virtual sphere. However, such update of the type information is not performed for the voxels occupied by the parent virtual sphere, i.e., the voxels assigned with the type information of the value 3. In other words, the voxel occupied by both the parent virtual sphere and the child virtual sphere in overlapping relation is assigned with the type information representing the parent virtual sphere. After placing one child virtual sphere, the processing subsequent to the step S270 is executed. Thus, the child virtual sphere having the diameter Rb is placed successively by repeating the step S280 until it is determined that the child virtual sphere having the diameter Rb cannot be placed. Overlapping between the child virtual spheres is allowed. Stated in another way, it is allowed that a voxel occupied by one child virtual sphere and a voxel occupied by another child virtual sphere overlap with each other.

If the step S270 determines that the child virtual sphere cannot be placed, the CPU 22 decrements the value of the diameter Rb by one (step S290), and then determines whether the diameter Rb is less than a minimum value Rbmin (step S300). If the diameter Rb is not less than the minimum value Rbmin, the CPU 22 executes the processing subsequent to the step S270. The minimum value Rbmin is a lower limit value of the diameter Rb of the child virtual sphere. Thus, the minimum value Rbmin is a threshold set with intent not to place the child virtual sphere having, for example, such a comparatively small diameter as hardly affecting the analysis result. In this embodiment, Rbmin is set to 2 $\mu$m.

If the diameter Rb is less than the minimum value Rbmin in the step S300, a virtual curved surface solid formed by the parent virtual sphere placed in the step S250 and the child virtual spheres placed in the step S280 is placed (step S310). More specifically, the type information corresponding to each of the voxels, which are occupied by the parent virtual sphere (i.e., the voxels assigned with the type information of the value 3) and by the child virtual spheres (i.e., the voxels assigned with the type information of the value 4), those voxels being contained in the porous body table 81 of the porous-body data 80 stored in the RAM 24 in the step S200, is updated to a value 5 indicating that the relevant voxel is a curved surface solid voxel occupied by the virtual curved surface solid. In addition, an identification code of the virtual curved surface solid is linked to the positional information of the curved surface solid voxel, which has been currently updated to the value 5. The identification code of the virtual curved surface solid is a value assigned to each of the virtual curved surface solids depending on, e.g., the order at which the virtual curved surface solids have been placed. The curved surface solid voxels constituting one virtual curved surface solid are assigned with the same identification code. After storing the information of the placed virtual curved surface solid in the RAM 24 (step S320), the CPU 22 determines whether 99% or more of the space voxels have been replaced with the curved surface solid voxels (step S330). More specifically, such determination is made by referring to the type information of the voxels contained in the porous body table 71, which is stored in the RAM 24, and by checking whether a rate of the number of the voxels assigned with the type information of the value 5 with respect to a total of the number of the voxels assigned with the type information of the value 0 and the voxels assigned with the type information of the value 5 is 99% or more. A threshold for the determination is not limited to 99%, and it may be set to a different value. If the step S330 determines that the rate of the voxels replaced with the curved surface solid voxels among the space voxels is less than 99%, the CPU 22 executes the processing subsequent to the step S230 and places the next virtual curved surface solid. On the other hand, if the step S330 determines that the rate of the voxels replaced with the curved surface solid voxels among the space voxels is 99% or more, the CPU 22 ends the virtual curved surface solid placement process.

In this embodiment, it is allowed that, when repeating the processing subsequent to the step S230 and placing the virtual curved surface solids successively, the voxel occupied by the virtual curved surface solid to be currently placed overlaps with the voxel occupied by the virtual curved surface solid having already been placed. More specifically, the placement of the parent virtual sphere is allowed in the step S230 of the virtual curved surface solid placement process even when, upon the placement of the parent virtual sphere having the diameter Ra, the placed parent virtual sphere overlaps with the virtual curved surface solid having already been placed. Stated in another way, if the parent virtual sphere having the diameter Ra does not overlap with the matter voxel, it is determined in the step S230 that the parent virtual sphere having the diameter Ra can be placed at the relevant position regardless of whether the relevant parent virtual sphere overlaps with the virtual curved surface solid having already been placed. Similarly, the placement of the child virtual sphere is allowed in the step S270 even when, upon the placement of the child virtual sphere having the diameter Rb, the placed child virtual sphere overlaps with the virtual curved surface solid having already been placed. Stated in another way, if the child virtual sphere having the diameter Rb does not overlap with the matter voxel, it is determined in the step S270 that the child virtual sphere having the diameter Rb can be placed at the relevant position regardless of whether the relevant child virtual sphere overlaps with the virtual curved surface solid having already been placed. As a result, the virtual curved surface solid having a volume as large as possible can be placed in comparison with the case of placing the virtual curved surface solid to be not overlapped with the other virtual curved surface solid.

Figure 8:
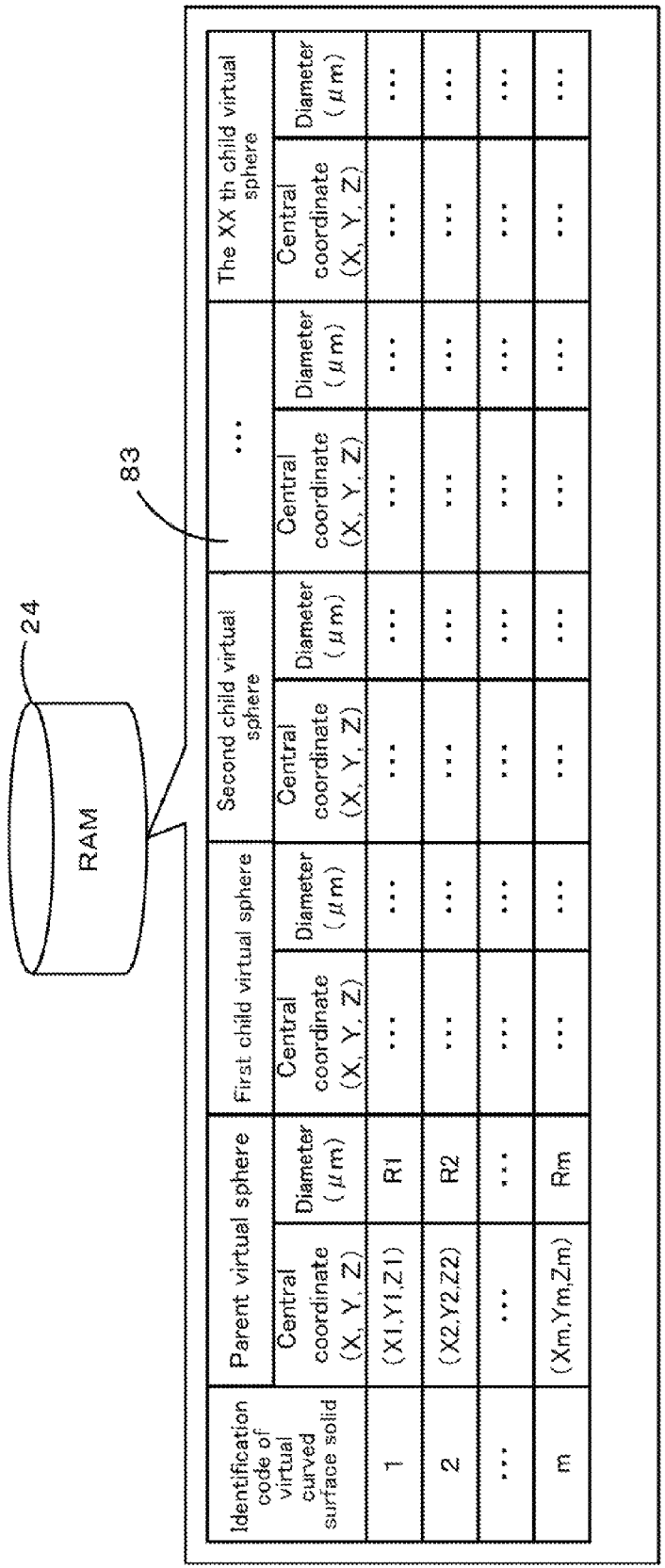
FIG. 8 is an illustration to explain one example of a virtual curved surface solid table 83.

In the step S320, a virtual curved surface solid table 83 representing information related to the virtual curved surface solids is stored, as part of the porous-body data 80, in the RAM 24, the virtual curved surface solid table 83 containing the identification code for identifying each virtual curved surface solid, the central coordinates (X, Y, Z) and the diameter of the parent virtual sphere constituting the virtual curved surface solid, and the central coordinates (X, Y, Z) and the diameter of one or more child virtual spheres constituting the virtual curved surface solid in linked relation. FIG. 8 illustrates one example of the virtual curved surface solid table 83. As illustrated in FIG. 8, for each of the plurality of virtual curved surface solids placed by repeating the steps S230 to S320, the virtual curved surface solid table 83 represents the identification code, the central coordinates and the diameter of the parent virtual sphere, and the central coordinates and the diameter of one or more child virtual spheres constituting the virtual curved surface solid in linked relation. Furthermore, since one virtual curved surface solid includes a plurality of child virtual spheres in some cases, the information regarding the plurality of child virtual spheres are stored, for example, in the order placed, such as the first child virtual sphere, the second child virtual sphere and so on, in an identifiably linked manner. It is to be noted that the virtual curved surface solid may include no child virtual spheres, namely it may be constituted only by the parent virtual sphere.

Figure 9A:
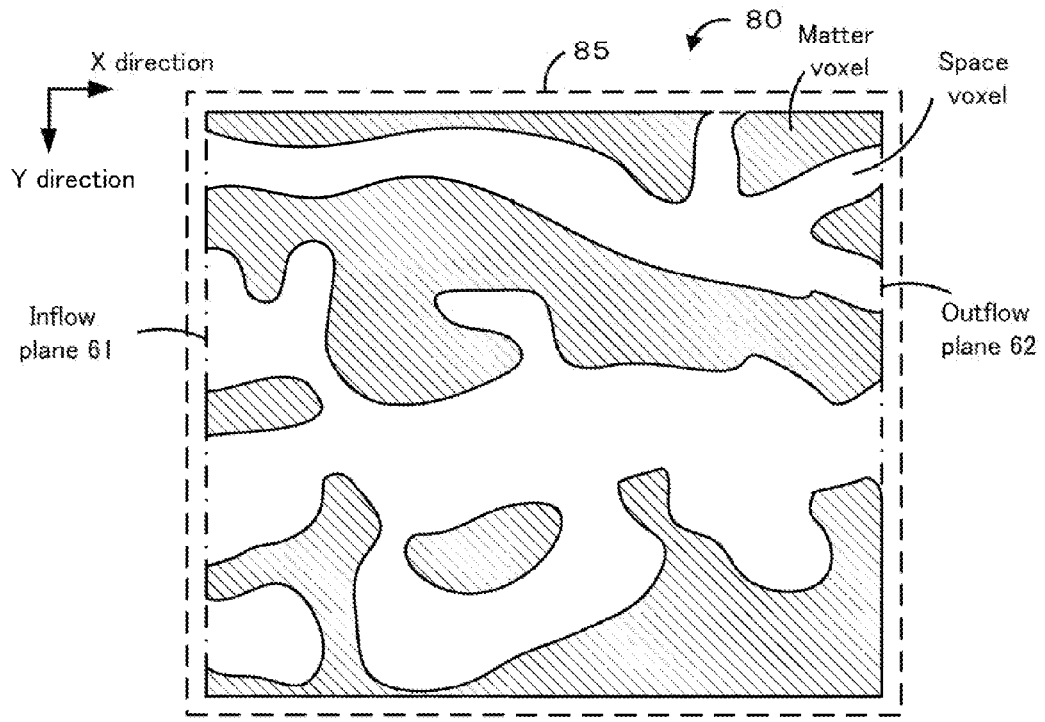
FIG. 9A and FIG. 9B are illustrations to explain placement of a parent virtual sphere.
Figure 9B:
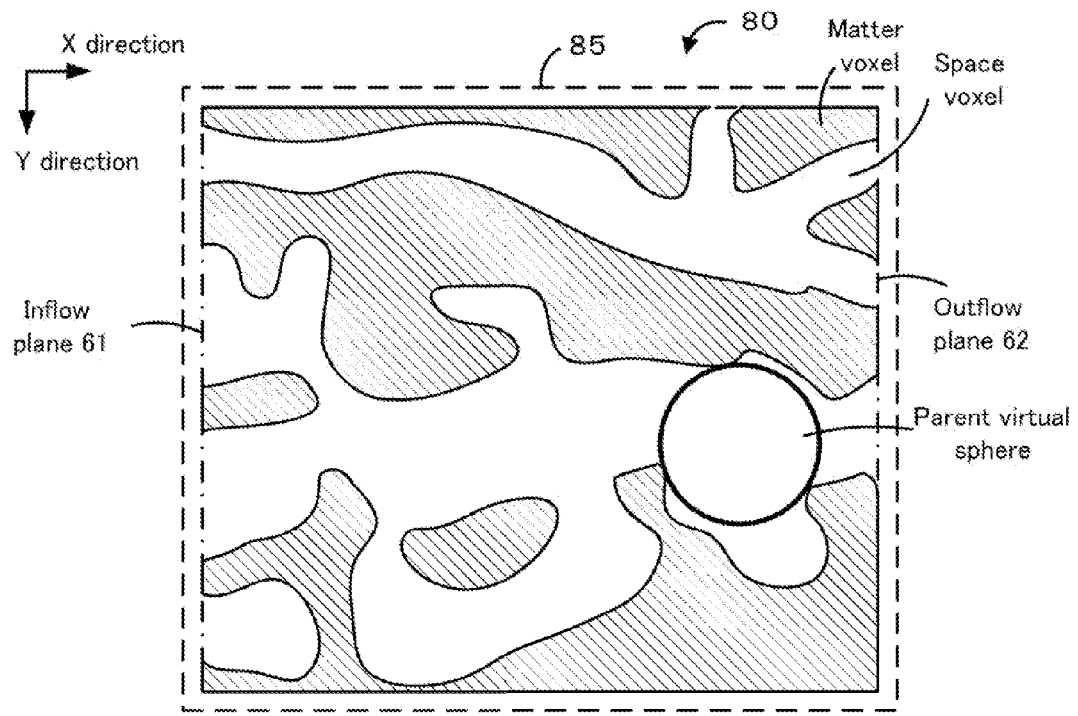
Figure 10A:
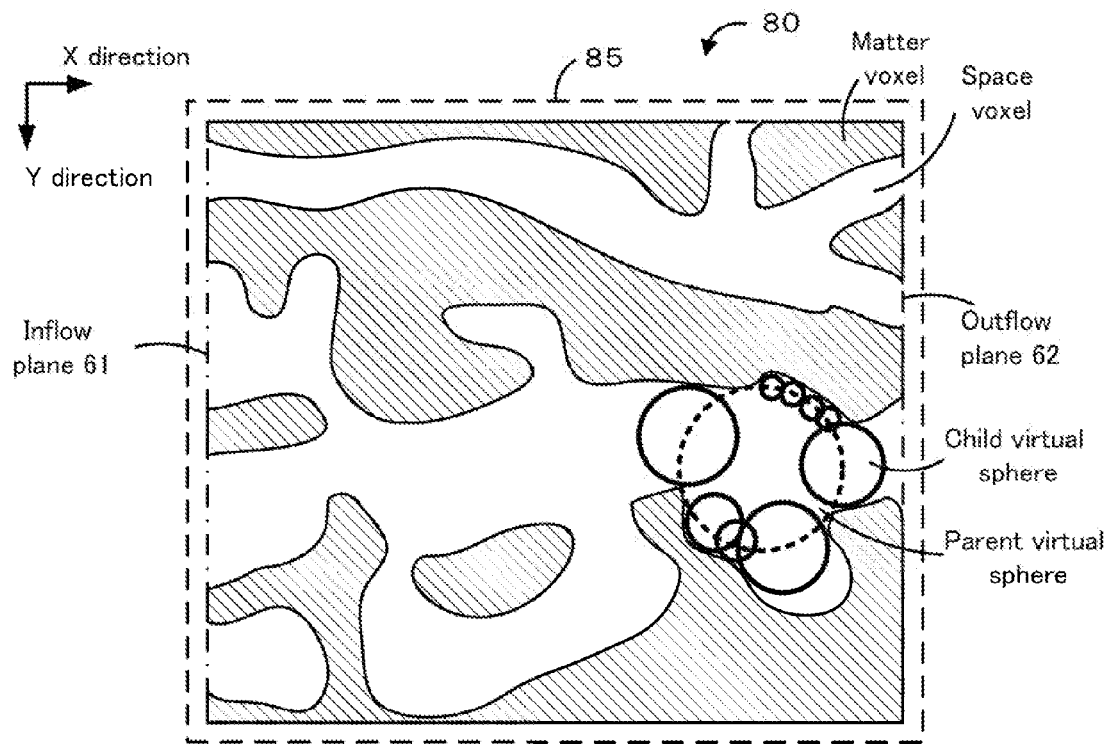
FIG. 10A and FIG. 10B are illustrations to explain placement of child virtual spheres and a virtual curved surface solid.
Figure 10B:
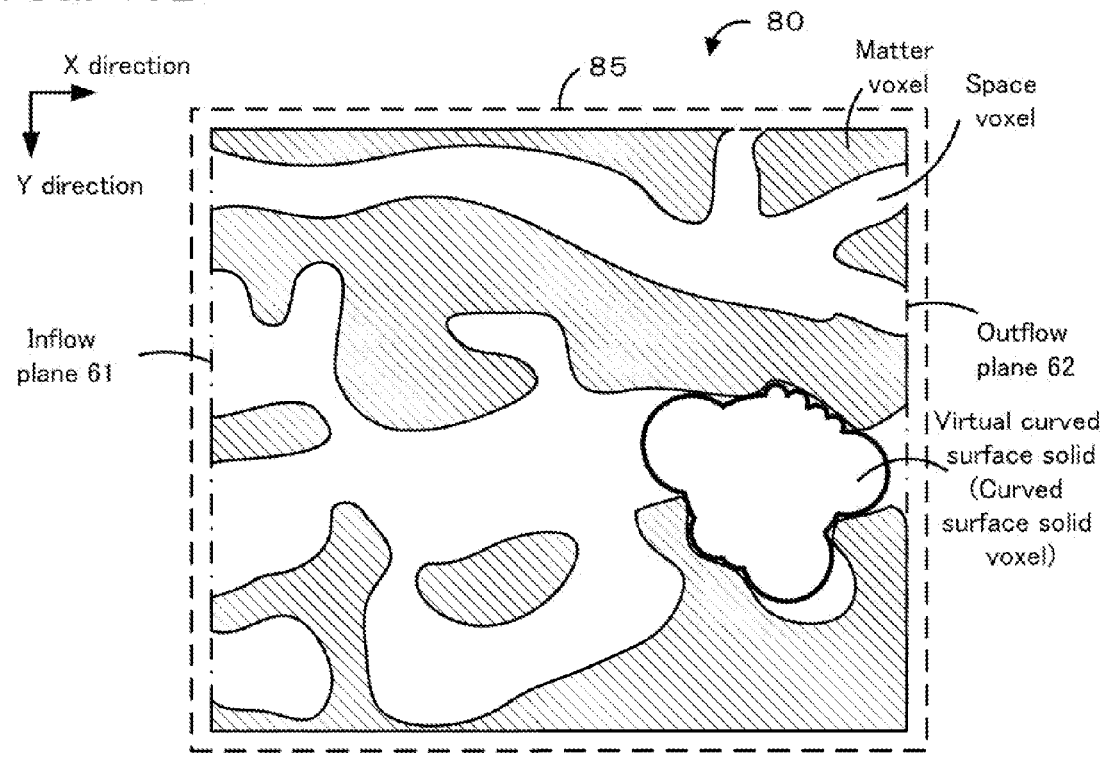

With the virtual curved surface solid placement process described above, the virtual curved surface solid table 83 is stored in the RAM 24, and the space voxels occupied by the placed virtual curved surface solids are replaced with the curved surface solid voxels. A manner of placing one virtual curved surface solid, formed by the parent virtual sphere and the child virtual spheres, through the virtual curved surface solid placement process is described here. FIG. 9A and FIG. 9B are illustrations to explain the placement of the parent virtual sphere, and FIG. 10A and FIG. 10B are illustrations to explain the placement of the child virtual spheres and the virtual curved surface solid. For convenience of the explanation, FIGS. 9 and 10 illustrate part of the porous-body data 80 corresponding to a section parallel to the X-direction, thus two-dimensionally depicting the placement of the virtual curved surface solid. FIG. 9A illustrates one example of the porous-body data 80 immediately after executing the step S210 and before placing the virtual curved surface solid. FIG. 9B illustrates a state after placing one parent virtual sphere. FIG. 10A illustrates a state after placing a plurality of child virtual spheres with respect to the parent virtual sphere placed in FIG. 9B. FIG. 10B illustrates a state after placing the virtual curved surface solid formed by the parent virtual sphere and the child virtual spheres. As illustrated in FIG. 9A, the porous-body data 80 is made up of the matter voxels and the space voxels, and it defines the inflow plane 61, the outflow plane 62, and virtual wall surfaces 85. The virtual curved surface solid (formed by the parent virtual sphere and the child virtual spheres) is placed within a range not exceeding outward from the virtual wall surfaces 85. Men the processing of the steps S220 to S250 is executed in such a state, one parent virtual sphere is placed (FIG. 9B) when, in the process of decrementing the value of the diameter Ra one by one, the diameter Ra becomes equal to a maximum diameter of the parent virtual sphere that can be placed in accordance with the porous-body data 80 within the range not overlapping with the matter voxel and not exceeding outward from the virtual wall surfaces 85, an condition of the diameter Ramax being set to a sufficiently large value. Then, by repeating the steps S270 to S300 until the step S300 determines that the diameter Rb is less than the minimum value Rbmin, plurality of child virtual spheres having different diameters are placed (FIG. 10A) such that respective centers of the child virtual spheres overlap with the parent virtual sphere, and that the voxels occupied by the child virtual spheres do not overlap with the matter voxels and they fill the space voxels. If the step S300 determines that the diameter Rb is less than the minimum value Rbmin, one virtual curved surface solid formed by the parent virtual sphere and the child virtual spheres, which have been placed so far, is placed (FIG. 10B). By repeating the processing of the steps S230 to S320 to place one virtual curved surface solid as described above until the step S330 determines that the rate of the voxels replaced with the curved surface solid voxels among the space voxels is 99% or more, other virtual curved surface solids are placed one by one in the other space voxels where any virtual curved surface solid is not yet placed, thereby successively filling the space voxels with the curved surface solid voxels. As a result, since a complicatedly-shaped space (pore) inside a porous body is replaced with the virtual curved surface solids each having a shape in combination of plurality of spheres, the spaces inside the porous body can be simulated by an assembly of the plurality of virtual curved surface solids with higher accuracy.

Return to the description of the analysis processing routine of FIG. 6. After the end of the virtual curved surface solid placement process in the step S100, the CPU 22 executes a fluid analysis process by performing a fluid analysis based on the porous-body data 80 stored in the RAM 24, and deriving information regarding the flow rate for each space voxel when a fluid passes through the porous body (step S110). It is assumed here that the fluid analysis process is performed by the known lattice Boltzmann method. More specifically, the fluid analysis is performed by the lattice Boltzmann method using a specific relation formula that, assuming a center point of each voxel in the porous-body data 80 to be each lattice point, expresses a fluid flow between each lattice point and another lattice point adjacent to the former when the fluid flows into the porous body from the inflow plane 61. As information regarding the flow rate for each space voxel, a flow rate vector defined by the flow rate and the flow direction is derived per space voxel in the porous-body data 80, and the derived flow rate vector per space voxel is stored in the porous body table 81, which is contained in the porous-body data 80 stored in the RAM 24, in linked relation. The fluid analysis is performed by employing respective numerical values of an average flow rate $T_{in}$ of the fluid at the inflow plane 61, a viscosity of the fluid, a density ρ of the fluid, etc., which are necessary for the analysis and which are previously stored in the HD 25, for example. Those numerical values may be set by the user through the input device 27. Here, the average flow rate $T_{in}$ is an average value of the flow rate immediately before the fluid enters the porous body, and it corresponds to an initial value of the flow rate in the fluid analysis. In this embodiment, the average flow rate $T_{in}$ is set to 0.01 m/sec. It is further assumed that the fluid is air at 0° C. under 1 atm, the viscosity μ is $1.73 \times 10^{-5}$ [Pa·s], and the density ρ is 1.25 [kg/m$^3$]. The fluid analysis process in the step S110 is executed by regarding the curved surface solid voxels as the space voxels without taking into consideration the virtual curved surface solid that has been placed in the step S100. While, in this embodiment, the fluid analysis process in the step S110 is executed in accordance with the porous-body data 80 stored in the RAM 24, it may be executed in accordance with the porous-body data 60 stored in the HDD 25.

Next, the CPU 22 executes a flow-rate-weighted mean diameter evaluation process of deriving a flow-rate-weighted mean diameter Ru, making good/no-good determination based on a derived value, and evaluating the trapping performance of the porous body (step S120). The flow-rate-weighted mean diameter evaluation process is executed by employing both the information regarding the plurality of virtual curved surface solids, which have been placed in the step S100, and the information regarding the flow rate, which has been derived by the fluid analysis in the step S10. The flow-rate-weighted mean diameter Ru is derived from the following formula (1). In this embodiment, the unit of the flow-rate-weighted mean diameter Ru is [μm], the unit of an equivalent diameter R'$_i$ is [μm], the unit of a volume V$_i$ is [cc], and the unit of an average flow rate U$_i$ is [mm/s].

[Math. 1]

$$Ru = \frac{\sum_{i=1}^{n}(R'_i \times V_i \times U_i)}{\sum_{i=1}^{n}(V_i \times U_i)}$$ formula (1)

Where,
Ru: flow-rate-weighted mean diameter
n: number of virtual curved surface solids that have been placed
R'$_i$: equivalent diameter of each virtual curved surface solid (i=i, 2, . . . , n)
V$_i$: volume of each virtual curved surface solid (i=1, 2, . . . , n)
U$_i$: average flow rate of fluid passing through each virtual curved surface solid (i=1, 2, . . . , n).

In the above formula, the number n of placed virtual curved surface solids is equal to a total number of the virtual curved surface solids that have been placed in the virtual curved surface solid placement process of the step S100. The equivalent diameter R'$_i$, the volume V$_i$, and the average flow rate U$_i$ for each virtual curved surface solid are derived, for example, as follows. First, one of the virtual curved surface solids is selected, and the curved surface solid voxels corresponding to the identification code of the selected virtual curved surface solid are checked by referring to the porous body table 81 in the RAM 24. Then, the number of voxels of curved surface solid voxels constituting the selected virtual curved surface solid is derived, and the product of the number of voxels and the volume (1.728 μm$^3$ in this embodiment) of one curved surface solid voxel is obtained as the volume V$_i$. Furthermore, a surface area S$_i$ of the selected virtual curved surface solid is derived from the information (i.e., the central coordinates and the diameters of the parent virtual sphere and the child virtual spheres) contained in the virtual curved surface solid table 83. Then, the equivalent diameter R'$_i$ is derived from a formula of (equivalent diameter R'$_i$)=6×(volume V$_i$ of the virtual curved surface solid)/(surface area S$_i$ of the virtual curved surface solid). Moreover, a flow rate Q$_i$ of the fluid passing through the selected virtual curved surface solid per unit time is derived, and the average flow rate U$_i$ is derived from a formula of (average flow rate U$_i$)=Q$_i$/{π(R'$_i$)$^2$/4}.

In this embodiment, overlapping between voxels occupied by different virtual curved surface solids is allowed. Therefore, the volume V$_i$ used in the above-mentioned formula (1) is preferably given as a value that is modified by assuming the voxel occupied by plurality of virtual curved surface solids (namely, the curved surface solid voxel existing as a component of plurality of virtual curved surface solids) to be occupied by only one virtual curved surface solid. In this embodiment, the volume V$_i$ is modified by assuming the curved surface solid voxel, which exists as a component of plurality of virtual curved surface solids, to be a component of only one among the plurality of virtual curved surface solids, the one having the maximum equivalent diameter R'$_i$. A value resulting after the modification is used in the formula (1). The modification is performed, for example, as follows. First, the volume V$_i$ is derived without considering whether the curved surface solid voxel exists as a component of plurality of virtual curved surface solids (namely, by regarding the curved surface solid voxel as a component of each of the plurality of virtual curved surface solids). In other words, the volume V$_i$ before the modification is derived. The equivalent diameter R'$_i$ is then derived from the volume V$_i$ before the modification. Thereafter, respective volumes V$_i$ of the virtual curved surface solids are successively derived again starting from the virtual curved surface solid having the maximum equivalent diameter $R'_i$ in descending order. At that time, the curved surface solid voxel that has been used once to derive the volume $V_i$ is not used to derive the volume $V_i$ of any other virtual curved surface solid (namely, the relevant voxel is not counted as the number of voxels of curved surface solid voxels constituting the virtual curved surface solid). As a result, it is possible to derive the volume $V_i$ (the volume $V_i$ after the modification) based on an assumption that the curved surface solid voxel, which exists as a component of plurality of virtual curved surface solids, to be a component of only one among the plurality of virtual curved surface solids, the one having the maximum equivalent diameter $R'_i$. The volume $V_i$ after the modification is then used in the formula (1). The equivalent diameter $R'_i$ may be given as the value derived from the volume $V_i$ before the modification, and it is not needed to be derived again from the volume $V_i$ after the modification.

The flow rate $Q_i$ of the passing fluid is derived, for example, as follows. First, among the curved surface solid voxels constituting the selected virtual curved surface solid, the curved surface solid voxels constituting the surface of the relevant virtual curved surface solid are specified in accordance with the information contained in the virtual curved surface solid table 83. The curved surface solid voxels constituting the surface of the virtual curved surface solid may be specified, for example, by finding, among the curved surface solid voxels constituting the selected virtual curved surface solid, the curved surface solid voxels each of which is adjacent to one of the space voxel, the matter voxel, and the curved surface solid voxel constituting the other virtual curved surface solid. Alternatively, the curved surface solid voxels constituting the surface of the virtual curved surface solid may be specified from the central coordinates and the diameters of the parent virtual sphere and the child virtual spheres, which are contained in the virtual curved surface solid table 83. Thereafter, the flow rate vector linked to each of the curved surface solid voxels constituting the surface of the virtual curved surface solid is checked by referring to the porous body table 81 in the RAM 24, and the curved surface solid voxels each corresponding to the flow rate vector, which is directed toward the inside of the virtual curved surface solid, are specified. The magnitudes of the flow rate vectors of the specified curved surface solid voxels are determined for each curved surface solid voxel. The flow rate $Q_i$ of the passing fluid is then derived from a formula of (flow rate $Q_i$ of the passing fluid per unit time)=(sum of the magnitudes of the flow rate vectors)× (among the curved surface solid voxels constituting the surface of the virtual curved surface solid, the number of curved surface solid voxels each linked to the flow rate vector that is directed to the inside of the virtual curved surface solid)× (surface area of one of the curved surface solid voxels (=1.44 $\mu m^2$)).

The CPU 22 derives the equivalent diameter $R'_i$, the volume $V_i$, and the average flow rate $U_i$, for each of the number n of virtual curved surface solids, as described above, and further derives the flow-rate-weighted mean diameter Ru from the above-mentioned formula (1). Then, the CPU 22 determines the trapping performance of the porous body (specifically, the region 50 of the porous partition wall 44), from which the porous-body data 60 has been obtained, to be good when the derived value of the flow-rate-weighted mean diameter Ru is not less than 10 µm and not more than 20 µm. Moreover, the CPU 22 determines that the trapping performance is not good when otherwise. The CPU 22 stores, in the RAM 24, the value of the flow-rate-weighted mean diameter Ru, the result of the good/no-good determination, and so on.

Next, the CPU 22 executes a difference ΔR evaluation process of deriving a difference ΔR, i.e., an absolute value of the difference between an arithmetic mean diameter Rc and the flow-rate-weighted mean diameter Ru, making good/no-good determination based on a derived value, and evaluating the performance of the porous body (step S130). This process is executed by employing both the information regarding the plurality of virtual curved surface solids, which have been placed in the step S100, and the flow-rate-weighted mean diameter Ru, which has been derived in the step S120. The difference ΔR is derived as follows. First, the arithmetic mean diameter $Rc=(R'_1+R'_2+\ldots+R'_n)/n$ is derived. The arithmetic mean diameter Rc may be derived by calculating each equivalent diameter $R'_i$ in a similar manner to that in the step S120, or by employing the value of each equivalent diameter $R'_i$, which has been derived in the step S120. The difference ΔR is then derived as difference $\Delta R=|Ru-Rc|$. The CPU 22 determines the trapping performance of the porous body (specifically, the region 50 of the porous partition wall 44), from which the porous-body data 60 has been obtained, to be better when the determination result of the flow-rate-weighted mean diameter evaluation process in the step S120 is good and when a value of the derived difference ΔR is not more than 2 µm. Furthermore, the CPU 22 determines the trapping performance to be not "better" when otherwise. Thus, in this embodiment, when the determination result in the step S120 is good (namely, the value of the flow-rate-weighted mean diameter Ru is not less than 10 µm and not more than 20 µm) and when the determination result in the step S130 is good (namely, the value of the difference ΔR is not more than 2 µm), the trapping performance of the porous body is determined to be "better". When the determination result in the step S120 is good, but when the determination result in the step S130 is not good, the trapping performance of the porous body is determined to be "good". When the determination result in the step S120 is not good, the trapping performance of the porous body is determined to be "no good" irrespective of the result of the step S130. The CPU 22 stores the value of the arithmetic mean diameter Rc, the value of the difference ΔR, the result of the good/no-good determination, etc. in the RAM 24.

After executing the various evaluation processes in the steps S120 to S130, the CPU 22 executes an analysis result output process of outputting, as analysis result data, the information stored in the RAM 24 in those processes, etc. and storing the output data in the HDD 25 (step S140). The CPU 22 then ends the analysis processing routine. The analysis result data contains, e.g., the porous-body data 80 including the porous body table 81, the inflow-outflow table 82, and the virtual curved surface solid table 83, which have been stored in the RAM 24, the value of the flow-rate-weighted mean diameter Ru and the result of the good/no-good determination, which have been derived in the step S120, as well as the value of the arithmetic mean diameter Rc, the value of the difference ΔR, the result of the good/no-good determination, which have been derived in the step S130. The analysis result data may further contain the values of the equivalent diameter $R'_i$, the volume $V_i$, the average flow rate $U_i$, etc., which have been used in the processing executed in the steps S120 to S130, and the average flow rate $T_{in}$, the viscosity µ of the fluid, the density ρ of the fluid, etc., which have been used in the fluid analysis process in the step S110.

Here, the correspondence relation between the components of this embodiment and the microstructure analysis apparatus of the present invention is explained. The RAM 24 and the HID 25 in this embodiment correspond to storage device in the present invention. The controller 21 executing the virtual curved surface solid placement process in the step S100 corresponds to virtual curved surface solid placement device. The controller 21 executing the fluid analysis process in the step S110 corresponds to fluid analysis device. The controller 21 executing the flow-rate-weighted mean diameter evaluation process and the difference ΔR evaluation process in the steps S120 and S130, respectively, corresponds to microstructure analysis device. In addition, this embodiment is intended to clarify one example of the microstructure analysis method of the present invention by explaining the operation of the user's PC 20.

According to the embodiment described in detail above, the controller 21 first refers to the porous-body data 80 representing positional information and voxel-type information in linked relation, and places a plurality of virtual curved surface solids, each of which is a curved surface solid in combination of a plurality of virtual spheres, in a way of filling the space voxels with the curved surface solid voxels that are occupied by the virtual curved surface solids. Then, the controller 21 executes the fluid analysis based on the porous-body data 80, and derives information regarding the flow rate for each space voxel when the fluid passes through the porous body. In accordance with the information regarding the virtual curved surface solids and the information regarding the fluid rate for each space voxel, the controller 21 derives the flow-rate-weighted mean diameter Ru that is a weighted average calculated by weighting the equivalent diameter $R'_i$ for each virtual curved surface solid with the volume $V_i$ and the average flow rate $U_i$ for each virtual curved surface solid. Here, as the volumes $V_i$ and the average flow rates $U_i$ in the plurality of placed virtual curved surface solids vary to a larger extent among the plurality of virtual curved surface solids, the value of the flow-rate-weighted mean diameter Ru tends to be excessively large or small. In a pore of the porous body, the pore being simulated by the virtual curved surface solid having a large value of the volume $V_i$, there is a tendency that a contact rate of the passing fluid with respect to the wall surface of the porous body reduces. In a pore of the porous body, the pore being simulated by the virtual curved surface solid having a small value of the volume $V_i$, there is a tendency that the fluid is harder to pass through the pore, and that a catalyst coated over the wall surface of the pore to employ the porous body as a filter is not coated properly. In a pore of the porous body, the pore being simulated by the virtual curved surface solid having the average flow rate $U_i$ higher than an average flow rate (simple average flow rate) for all the pores (=all the space voxels) in the porous body, there is a tendency that the pore is less contributable to the trapping performance because the fluid passes through the pore in a shorter time. In a pore of the porous body, the pore being simulated by the virtual curved surface solid having the average flow rate $U_i$ lower than the average flow rate (simple average flow rate) for all the pores (=all the space voxels) in the porous body, there is a tendency that the pore is less contributable to the trapping performance because the inflow amount of the fluid is small. Thus, the pore of the porous body, which is simulated by the virtual curved surface solid having a too large or small value of the volume $V_i$ or a too high or low value of the average flow rate $U_i$, tends to be less contributable to the trapping performance. Stated in another way, in the porous body in which the pores being less contributable to the trapping performance occupy a large part, the derived value of the flow-rate-weighted mean diameter Ru tends to be too large or too small. Hence the trapping performance of the porous body can be analyzed with relatively high accuracy by deriving the flow-rate-weighted mean diameter Ru. Further, the trapping performance of the porous body can be evaluated with relatively high accuracy by making the good/no-good determination based on the value of the flow-rate-weighted mean diameter Ru. Alternatively, the trapping performance of the porous body can be estimated with relatively high accuracy based on the value of the flow-rate-weighted mean diameter Ru.

In addition, the controller 21 derives the difference ΔR that is an absolute value of the difference between the arithmetic mean diameter Rc and the flow-rate-weighted mean diameter Ru. Here, when the flow-rate-weighted mean diameter Ru takes a comparable value, the trapping performance of the porous body tends to be higher as the absolute value of the difference between the arithmetic mean diameter Rc and the flow-rate-weighted mean diameter Ru reduces. Accordingly, the trapping performance of the porous body can be analyzed with higher accuracy by deriving the difference ΔR in the microstructure analysis. In addition, the trapping performance of the porous body can be evaluated with higher accuracy by making the good/no-good determination based on the value of the difference ΔR. Alternatively, the trapping performance of the porous body can be estimated with higher accuracy based an the value of the difference ΔR.

Moreover, the controller 21 executes the processing on the porous-body data 80 through the steps of placing one parent virtual sphere with a maximum diameter among the parent virtual spheres, which can be placed in a way of not overlapping with any matter voxel and filling the space voxels, placing one or more child virtual spheres such that a center of each child virtual sphere overlaps with the placed parent virtual sphere, and that voxels occupied by each child virtual sphere do not overlap with the matter voxel and fill the space voxels, and placing one virtual curved surface solid, which is formed by the parent virtual sphere and the child virtual spheres, in a way of filling the space voxels with the curved surface solid voxels that are voxels occupied by the virtual curved surface solid. The above-mentioned processing is repeated to place the virtual curved surface solid in plurality of number while allowing voxels occupied by different virtual curved surface solids to be overlapped with each other. Thus, since the virtual curved surface solid is placed such that the curved surface solid voxels do not overlap with any matter voxel, a processing time necessary for placing the virtual curved surface solids can be shortened in comparison with the case of allowing the overlapping between the curved surface solid voxels and the matter voxels. Further more, since the parent virtual sphere with the maximum diameter among the parent virtual spheres, which can be placed on the above-mentioned condition, is placed, the space voxels can be filled with the virtual curved surface solids having the volumes $V_i$ as large as possible.

There is a tendency that, as the thickness of the porous body (i.e., the length of the porous body in the direction perpendicular to the inflow plane through which fluid flows into the porous body) reduces, change of the trapping performance due to variation in the pore volume inside the porous body and variation in the flow rate inside the pores is more significant. Also, as the thickness of the porous body reduces, the trapping performance is more apt to lower. Therefore, the significance of using the flow-rate-weighted mean diameter Ru and the difference ΔR is greater particularly when the trapping performance of the porous body with a small thickness (e.g., a thickness of 4 to 6 mil) is to be evaluated.

As a matter of course, the present invention is not limited to the above-described embodiment, and the present invention can be practiced in various forms within the range belonging to the technical scope of the present invention.

For instance, while the difference ΔR evaluation process in the above-described embodiment is executed to derive the difference ΔR and to make the good/no-good determination, the good/no-good determination may be omitted. Furthermore, the step S130 may be omitted.

While the flow-rate weighted mean diameter evaluation process in the above-described embodiment is executed to derive the flow-rate-weighted mean diameter Ru and to make the good/no-good determination, the good/no-good determination may be omitted.

While, in the above-described embodiment, the arithmetic mean diameter Rc is derived as the arithmetic mean diameter $Rc=(R'_1+R'_2+\ldots+R'_n)/n$, the arithmetic mean diameter Rc is just required to represent an average diameter of the pores in the case of not performing the weighting with, e.g., the flow rate $U_i$ and the volume $V_i$. For instance, a value of the average pore diameter measured by the mercury press-in method may be used as the arithmetic mean diameter Rc. In such a case, the value of the average pore diameter previously measured by the mercury press-in method may be contained in the porous-body data 60 and stored in the HDD 25 for use in the difference ΔR evaluation process.

While, in the above-described embodiment, the fluid analysis process is executed after the virtual curved surface solid placement process, the fluid analysis process may be executed before the virtual curved surface solid placement process. Alternatively, both the processes may be executed in parallel.

While, in the above-described embodiment, the virtual curved surface solid placement process is executed by placing one parent virtual sphere for one virtual curved surface solid, a plurality of parent virtual spheres may be placed. When the parent virtual sphere is placed in plurality of number, the virtual curved surface solid may be formed by the plurality of parent virtual spheres and one or more child virtual spheres each of which occupies voxels in partly overlapping relation to the voxels occupied by at least one of the plurality of parent virtual spheres. Alternatively, one virtual curved surface solid may be formed by one virtual sphere (one parent virtual sphere in this embodiment) without placing any child virtual spheres. In such a case, the equivalent diameter $R'_i$ may be simply given as the diameter of the one virtual sphere. However, it is preferable to place the virtual curved surface solid, which is formed by a combination of plurality of virtual spheres, for the reason that a complicatedly-shaped space (pore) in the porous body can be simulated with higher accuracy.

While, in the above-described embodiment, the virtual curved surface solid placement process is executed on condition of, when a plurality of child virtual spheres is placed in the process of placing one virtual curved surface solid, allowing the plurality of child virtual spheres to be overlapped with each other, the plurality of child virtual spheres may be placed on condition of not allowing them to be overlapped with each other.

While, in the above-described embodiment, the virtual curved surface solid placement process is executed by placing the child virtual sphere such that the center of the child virtual sphere overlaps with the parent virtual sphere, the placement of the child virtual sphere is not limited to such a case. It is just required that the voxels occupied by the child virtual sphere and the voxels occupied by the parent virtual sphere overlap with each other in part.

While, in the above-described embodiment, the virtual curved surface solid is placed such that the curved surface solid voxels do not overlap with any matter voxel, partial overlapping between the curved surface solid voxels and the matter voxels may be allowed.

While, in the above-described embodiment, the fluid analysis is performed by the lattice Boltzmann method, other fluid analysis methods may also be used optionally.

While, in the above-described embodiment, the product of the number of voxels of curved surface solid voxels constituting the virtual curved surface solid and the volume (1.728 $\mu m^3$ in the embodiment) of one curved surface solid voxel is obtained as the volume $V_i$ when deriving the equivalent diameter $R'_i$ (=6×volume $V_i$ of the virtual curved surface solid/surface area $S_i$ of the virtual curved surface solid), the present invention is not limited to such a case. For instance, the volume $V_i$ of the virtual curved surface solid may be derived in accordance with the information (respective central coordinates and diameters of the parent virtual sphere and child virtual spheres) contained in the virtual curved surface solid table 83. In other words, the volume $V_i$ may be given as a volume resulting in the case of regarding the virtual curved surface solid to be an assembly of the parent virtual sphere and child virtual spheres, which are defined by their central coordinates and diameters, (namely in the case where edges of the virtual curved surface solid are represented by curved lines and curved surfaces), instead of a volume resulting in the case of regarding the virtual curved surface solid to be an assembly of the space voxels (namely in the case where edges of the virtual curved surface solid are represented by edges of the space voxels, i.e., linear lines and flat surfaces).

While, in the above-described embodiment, the equivalent diameter $R'_i$ is derived from the formula of (equivalent diameter $R'_i$=6×volume $V_i$ of the virtual curved surface solid/surface area $S_i$ of the virtual curved surface solid), the present invention is not limited to such a case. Thus, the equivalent diameter $R'_i$ is not limited to the value obtained from the above formula insofar as it represents a diameter resulting when the virtual curved surface solid is converted to one sphere. For instance, the diameter of a sphere having the same volume as the volume $V_i$ of the virtual curved surface solid may be used as the equivalent diameter $R'_i$.

While, in the above-described embodiment, the average flow rate $U_i$ is derived from the formula of $U_i=Q_i/\{\pi(R'_i)^2/4\}$, the present invention is not limited such a case. For instance, the average flow rate $U_i$ may be derived by deriving average flow rate components $U_{xi}$, $U_{yi}$ and $U_{zi}$ of the virtual curved surface solid in the X-, Y- and Z-directions, and by calculating an average flow rate $U_i=\sqrt{(U_{xi}^2+U_{yi}^2+U_{zi}^2)}$. In that case, an average flow rate component $U_{xi}$ is derived as follows. First, for the virtual curved surface solid from which the average flow rate $U_i$ is to be derived, a section passing the center of the parent virtual sphere of the relevant virtual curved surface solid and being perpendicular to the X-direction is specified, and curved surface solid voxels constituting the relevant section are specified. Then, X-directional components of flow rate vectors linked respectively to the specified curved surface solid voxels (i.e., the magnitudes of the relevant flow rate vectors in the X-direction) are checked by referring to the porous body table 81, and an average value of those X-directional components is calculated as the average flow rate component $U_{xi}$. Similarly, curved surface solid voxels constituting a section, which passes the center of the parent virtual sphere of the relevant virtual curved surface solid and which is perpendicular to the Y-direction, are specified. Then, an average value of Y-directional components of flow rate vectors linked respectively to the specified curved surface solid voxels is calculated as the average flow rate component $U_{yi}$. Furthermore, curved surface solid voxels constituting a section, which passes the center of the parent virtual sphere of the relevant virtual curved surface solid and which is perpendicular to the Z-direction, are specified. Then, an average value of Z-directional components of flow rate vectors linked respectively to the specified curved surface solid voxels is calculated as the average flow rate component $U_{zi}$.

While, in the above-described embodiment, the virtual curved surface solid placement process is executed on condition of allowing the voxels occupied by one virtual curved surface solid and another virtual curved surface solid to be overlapped with each other, those voxels may be set not to be overlapped with each other. In that case, the above-described step S230 of the virtual curved surface solid placement process in FIG. 7 may be executed to make determination as follows. When, upon the placement of the parent virtual sphere having the diameter Ra at some position, the parent virtual sphere does not overlap with any matter voxel and further does not overlap with the virtual curved surface solid having already been placed, the parent virtual sphere having the diameter Ra can be placed at the relevant position. Similarly, the step S270 may be executed to make determination as follows. When, upon the placement of the child virtual sphere having the diameter Rb at some position, the child virtual sphere does not overlap with any matter voxel and further does not overlap with the virtual curved surface solid having already been placed, the child virtual sphere having the diameter Rb can be placed at the relevant position. When the overlapping between the voxels occupied by two virtual curved surface solids is not allowed, the volume $V_i$ after the modification is no longer needed to be derived in the flow-rate-weighted mean diameter evaluation process of the step S120 in the above-described embodiment, and the volume $V_i$ derived before deriving the equivalent diameter $R'_i$ may be used, at it is, in the formula (1).

While, in the above-described embodiment, the centers of the parent virtual sphere and the child virtual sphere are each assumed to position at the center of the voxel, the present invention is not limited to such a case. The centers of the parent virtual sphere and the child virtual sphere are each just required to be positioned within the voxel. For instance, the centers of the parent virtual sphere and the child virtual sphere may be each positioned at an edge of the voxel, the edge being positioned closest to the origin of the X-, Y- and Z-coordinates.

While, in the above-described embodiment, the flow-rate-weighted mean diameter Ru is derived from the formula (1), the average flow rate $U_i$ in the numerator of the formula (1) may be replaced with an "absolute value of the difference between the average flow rate $U_i$ and an overall average flow rate" (=|average flow rate $U_i$–overall average flow rate|). Here, the overall average flow rate is a value obtained by deriving components of flow rate vectors of the curved surface solid voxels in the direction perpendicular to the inflow plane 61 (i.e., X-direction components of those flow rate vectors), and by averaging the X-direction components.

While, in the above-described embodiment, the determination result of "good" is resulted on condition that the flow-rate-weighted mean diameter Ru is not less than 10 μm and not more than 20 μm, the present invention is not limited such a case. A range where the determination result of "good" is resulted may be set as appropriate depending on the trapping performance demanded for the porous body, environments of the porous body in use, and so on. That point is similarly applied to the setting of the threshold (not more than 2 μm) that is used in the determination of the difference AR.

EXAMPLES

An example in which the analysis process program and the microstructure analysis apparatus were actually fabricated is described as Example. It is to be noted that the present invention is not limited to the following Example.

Example 1

An analysis process program having the functions of the above-described embodiment was fabricated as Example 1. Furthermore, a microstructure analysis apparatus of Example 1 was obtained by storing the analysis process program in a HDD of a computer provided with a controller and the HDD, the controller including a CPU, a RCM, and a RAM.

[Fabrication of Porous Bodies 1 to 8]

A porous body 1 in the form of a honeycomb filter including the porous partition walls 44 was fabricated as an object for analysis of microstructure. First, a base material was prepared by mixing SiC powder and metallic Si powder at a ratio of 80:20 by mass. A plastic green body was prepared by adding, to the base material, starch and resin foam as pore-forming materials, as well as methyl cellulose, hydroxypropoxyl methyl cellulose, a surfactant, and water. Then, the prepared green body was ejection-molded by employing a specific mold, and a molding (having an external shape of a rectangular prism) was obtained with the porous partition walls 44 formed therein in the shape illustrated in FIGS. 2 and 3. The obtained molding was dried by microwave waves and further dried by hot air. Thereafter, the molding was partly sealed and subjected to preliminary firing in an oxidative atmosphere at 550° C. for 3 hours. The molding was then subjected to main firing in an inert atmosphere of Ar at 1450° C. Sealed portions were formed by alternately masking opened cells at one end surface of the molding, and by dipping the masked end surface in sealing slurry (which was the same as the above-mentioned green body) such that opened portions and the sealed portions were alternately arrayed. Similarly, the other end surface of the molding was masked, and sealed portions were formed such that a cell having one opened end and the other sealed end and a cell having one sealed end and the other opened end were alternately arrayed. After grinding the molding subjected to the main firing into a cylindrical shape, it was coated with outer-periphery coating slurry, which was prepared by kneading alumina silicate fibers, colloidal silica, polyvinyl alcohol, SiC, and water. The outer peripheral protective portion 32 was formed by drying and hardening the coated slurry. A honeycomb filter made of the porous body 1 was thus obtained. Here, the honeycomb filter was in the form having a cross-section with a diameter of 143.8 mm and a length of 152.4 mm. The cell density was 300 cells/square inch, and the thickness of the partition wall was 12 mil. Other porous bodies 2 to 8 were further fabricated by employing the same materials and method as those used in fabricating the porous body 1.

[Fabrication of Porous Bodies 9 to 12]

Porous bodies 9 to 12 made of cordierite were fabricated by the same method as that used in fabricating the porous body 1 except for preparing the base material by mixing talc powder and alumina powder.

[Analysis of Microstructure]

Among voxel data obtained by CT-scanning the porous body 1, one set of data representing 300 μm (=1.2 μm×250 voxels) in the X-direction, which was the same value as the thickness of the porous body 1 through which exhaust gas passes, 480 μm (=1.2 μm×400 voxels) in the Y-direction, and 480 μm (=1.2 μm×400 voxels) in the Z-direction was extracted and stored, as the above-described porous-body data 60, in the HD in Example 1. The above-described analysis processing routine was executed on the porous-body data 60 in Example 1. Analysis result data containing the porous body table and the virtual curved surface solid table, as well as respective values of the flow-rate-weighted mean diameter Ru, the difference ΔR, the equivalent diameter R'$_i$, the volume V$_i$, and the average flow rate U$_i$ for each virtual curved surface solid, which have been described above, was obtained as the analysis result data of the analysis processing routine. Analysis result data was similarly obtained for each of the porous bodies 2 to 12.

[Measurement of Number of Leaked Particles]

For the porous bodies 1 to 12, the number of leaked particles was measured as a value indicating actual trapping performance. More specifically, the porous bodies 1 to 12 were each mounted to an exhaust pipe for exhaust gas of an automobile, and a diesel engine of the automobile was rotated in accordance with traveling specified as the NEDC (New European Driving Cycle) node, thus causing a fluid (engine exhaust gas) including particulates to pass through each porous body. Then, the number of particulates remaining in the fluid having passed through the porous body was measured as the number of leaked particles, and the number of leaked particles [number/km] after being converted to the number of leaked particles per 1 km of traveling distance was obtained as a value indicating the trapping performance.

[Evaluation of Trapping Performance Based on Flow-rate-Weighted Mean Diameter Ru and Difference ΔR]

Figure 11:
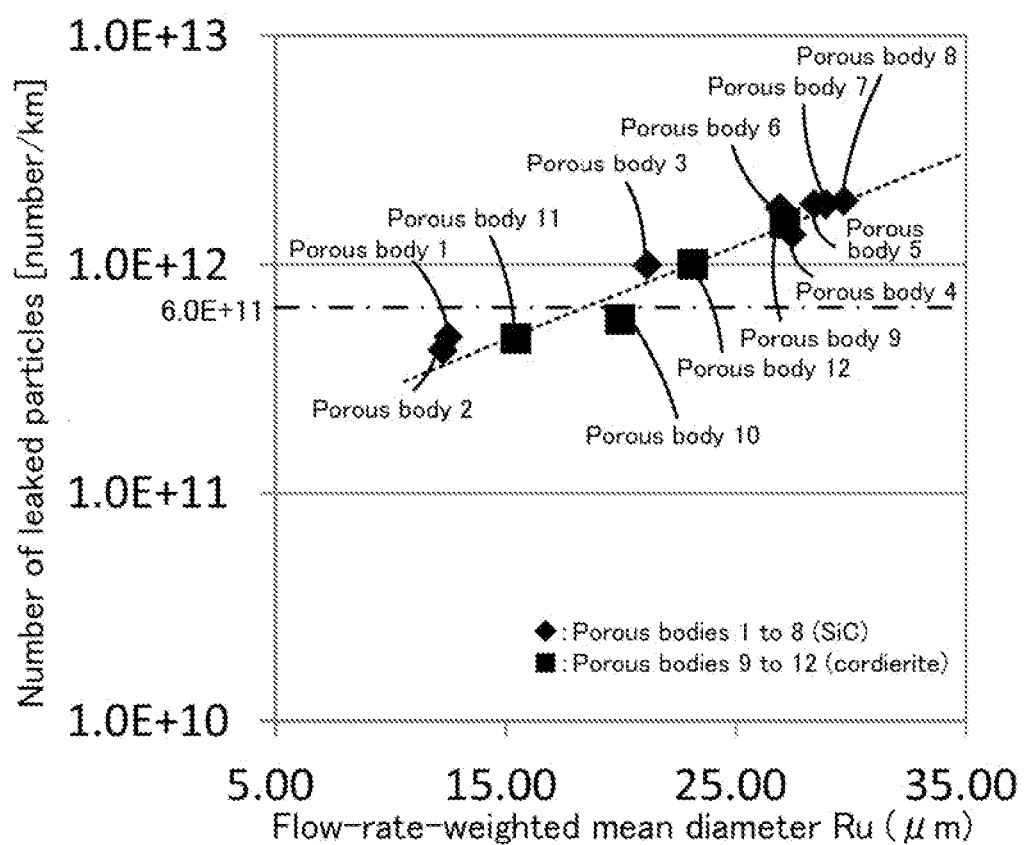
FIG. 11 is a graph depicting a relation between a flow-rate-weighted mean diameter Ru and the number of leaked particles for each of porous bodies 1 to 12.

Table 1 lists respective values of the flow-rate-weighted mean diameter Ru, the difference ΔR, and the number of leaked particles, which were obtained by executing the analysis processing routine on the porous bodies 1 to 12 in Example 1. FIG. 11 is a graph depicting a relation between the flow-rate-weighted mean diameter Ru and the number of leaked particles for each of the porous bodies 1 to 12. As seen from FIG. 11, in any of the porous bodies 1 to 12, the flow-rate-weighted mean diameter Ru is in the range of 10 μm to 30 μm, and the number of leaked particles reduces (namely, the trapping performance increases) as the flow-rate-weighted mean diameter Ru reduces. Furthermore, it is deemed that the number of leaked particles can be estimated from a value of the flow-rate-weighted mean diameter Ru by employing an approximation curve (denoted by a dotted line in FIG. 11) obtained from points plotted in FIG. 11. In addition, as seen from FIG. 11, although the materials of the porous bodies 1 to 8 and the porous bodies 9 to 12 are different, the relation between the flow-rate-weighted mean diameter Ru and the number of leaked particles can be expressed by almost the same approximation curve for all those porous bodies. Accordingly, it is understood that the trapping performance can be compared even between the porous bodies made of different materials by employing the flow-rate-weighted mean diameter Ru. Moreover, as seen from the approximation curve, when the flow-rate-weighted mean diameter Ru is not more than 20 μm, the exhaust gas restriction value for an automobile (Euro6 (from 2017)), i.e., the condition of the number of leaked particles being not more than 6×10$^{11}$ [number/km], is satisfied. It is hence deemed that whether the trapping performance is good or not good can be determined depending on whether the flow-rate-weighted mean diameter Ru is not more than 20 μm. As described above, when the flow-rate-weighted mean diameter Ru is too small, it is estimated that the trapping performance reduces and the number of leaked particles increases. As seen from FIG. 11, however, when the flow-rate-weighted mean diameter Ru is in the range of 10 μm or more, the trapping performance increases as the flow-rate-weighted mean diameter Ru reduces. Therefore, it is deemed that the trapping performance is satisfactory if the porous body has the flow-rate-weighted mean diameter Ru in the range of 10 μm to 20 μm. As seen from Table 1, comparing the porous bodies 4, 6 and 9 in which the values of the flow-rate-weighted mean diameter Ru are nearly equal, the number of leaked particles in the porous body 4 having a minimum value of the difference ΔR is smaller than that in the porous bodies 6 and 9. Thus, there is a similar tendency between a magnitude relation of the difference ΔR and a magnitude relation of the number of leaked particles. It is hence confirmed that, when the values of the flow-rate-weighted mean diameter Ru are nearly equal, the number of leaked particles tends to reduce (namely, the trapping performance tends to increase) as the difference ΔR reduces.

TABLE 1

| | materials | flow-rate-weighted mean diameter Ru [μm] | difference ΔR [μm] | number of leaked particles [number/km] |
|---|---|---|---|---|
| porous body 1 | SiC | 12.50 | 2.35 | 4.78E+11 |
| porous body 2 | SiC | 12.26 | 2.03 | 4.19E+11 |
| porous body 3 | SiC | 21.15 | 1.67 | 9.93E+11 |
| porous body 4 | SiC | 27.44 | 2.76 | 1.35E+12 |
| porous body 5 | SiC | 28.42 | 4.08 | 1.83E+12 |
| porous body 6 | SiC | 26.92 | 3.34 | 1.76E+12 |
| porous body 7 | SiC | 28.91 | 2.79 | 1.83E+12 |
| porous body 8 | SiC | 29.71 | 2.36 | 1.89E+12 |
| porous body 9 | cordierite | 27.14 | 3.24 | 1.52E+12 |
| porous body 10 | cordierite | 19.97 | 6.61 | 5.70E+11 |
| porous body 11 | cordierite | 15.43 | 3.62 | 4.71E+11 |
| porous body 12 | cordierite | 23.14 | 5.04 | 1.00E+12 |

[Relation Between Difference ΔR and Pore Distribution]

Figure 12:
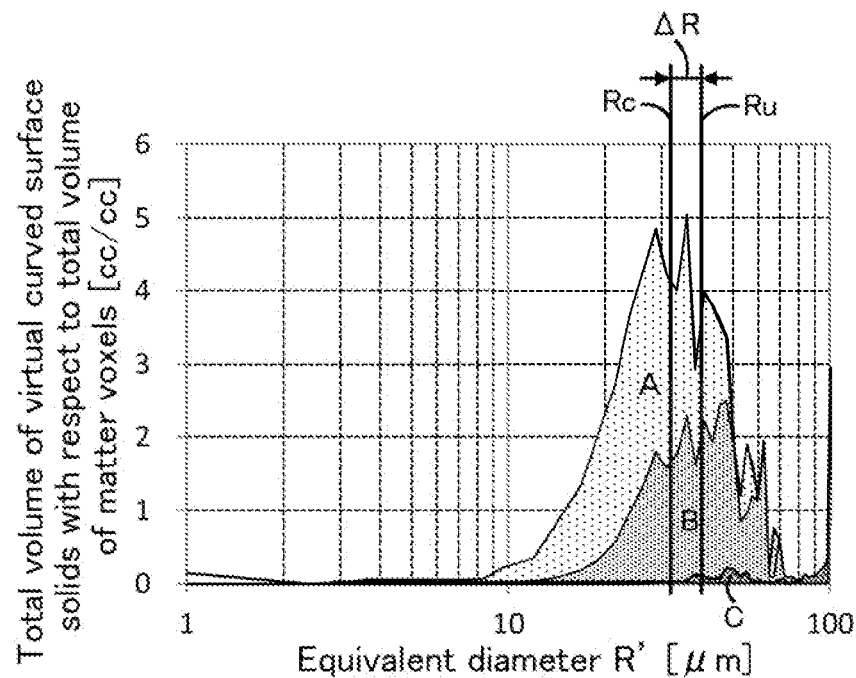
FIG. 12 is a graph depicting a log differential pore volume distribution of the porous body 13.
Figure 13:
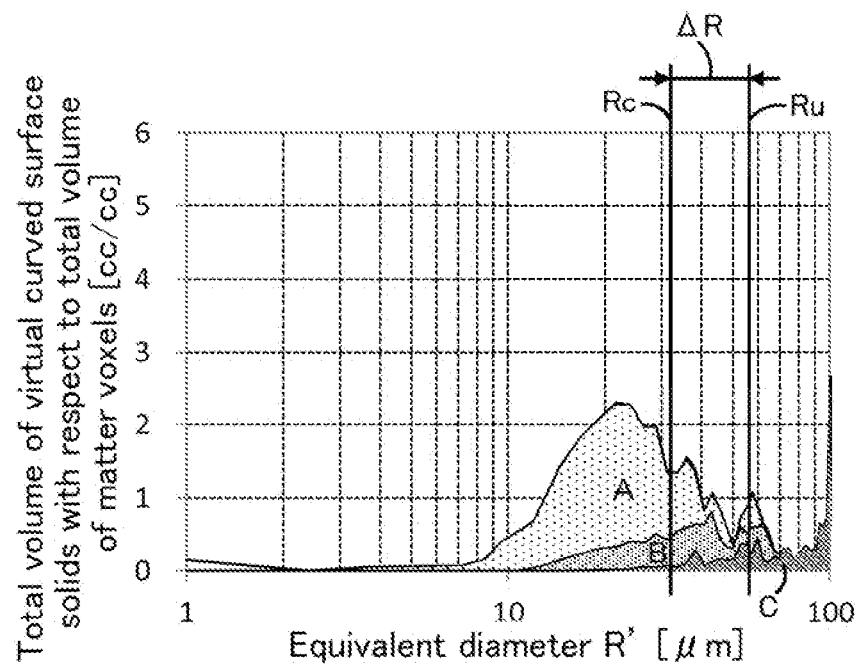
FIG. 13 is a graph depicting a log differential pore volume distribution of the porous body 14.

Porous bodies 13 and 14 made of cordierite were fabricated by a similar method to that used in fabricating the porous body 9. Analysis result data was obtained by executing the analysis processing routine in Example 1 on data obtained with the CT scan in a similar manner to that executed for the porous bodies 1 to 12. FIGS. 12 and 13 are graphs depicting respective pore distributions of the porous bodies 13 and 14. In each of FIGS. 12 and 13, the horizontal axis represents the equivalent diameter R' [μm] (in terms of common logarithm), and the vertical axis represents a log differential pore volume distribution expressed by a rate of the total volume of the virtual curved surface solids with respect to the total volume of the matter voxels [cc/cc](=(sun of the volumes V$_i$ of the virtual curved surface solids corresponding to the individual equivalent diameters R')/(sun of the volumes of all the matter voxels). In each of FIGS. 12 and 13, the virtual curved surface solids are classified into three groups depending on the value of the average flow rate U$_i$. More specifically, a region A in FIGS. 12 and 13 represents a distribution of the virtual curved surface solids in which the average flow rate U$_i$ is low (not less than 0 mm/s and less than 20 m/s), a region B represents a distribution of the virtual curved surface solids in which the average flow rate U$_i$ is medium (not less than 20 mm/s and less than 60 mm/s), and a region C represents a distribution of the virtual curved surface solids in which the average flow rate U$_i$ is high (not less than 60 mm/s). FIGS. 12 and 13 further indicate respective values of the flow-rate-weighted mean diameter Ru, the arithmetic mean diameter Rc, and the difference ΔR of the porous bodies 13 and 14. The flow-rate-weighted mean diameter Ru, the arithmetic mean diameter Rc, and the difference ΔR of the porous body 13 were respectively 40.3 μm, 32.9 μm, and 7.4 μm. The flow-rate-weighted mean diameter Ru, the arithmetic mean diameter Rc, and the difference ΔR of the porous body 14 were respectively 57.9 μm, 33.2 μm, and 24.7 μm. As seen from FIGS. 12 and 13, a proportion of the virtual curved surface solids having the average flow rate $U_i$ in the medium range is higher in the porous body 13 having a smaller value of the flow-rate-weighted mean diameter Ru. Moreover, although the values of the arithmetic mean diameters Rc are nearly equal in the porous bodies 13 and 14, the pore distribution is different between them as seen from FIGS. 12 and 13. It is hence understood that such a difference in the pore distribution can be quantified by deriving the flow-rate-weighted mean diameter Ru.

The present application claims priority from Japanese Patent Application No. 2014-072361 filed on Mar. 31, 2014, the entire contents of which are incorporated herein by reference.

What is claimed is:

1. A microstructure analysis method of a porous body using porous-body data in which positional information indicating position of a voxel obtained by three-dimensionally scanning the porous body is associated with voxel-type information indicating whether the voxel is a space voxel representing space or a matter voxel representing object, the method comprising the steps of:
   (a) a step of taking a curved surface solid formed by one virtual sphere or a combination of a plurality of virtual spheres as a virtual curved surface solid, and placing the plurality of virtual curved surface solids so as to fill in the space voxels with curved surface solid voxels which are voxels occupied by the virtual curved surface solid, referring to the porous-body data;
   (b) a step of deriving information regarding a flow rate for each of the space voxels when a fluid passes through the porous body by executing a fluid analysis based on the porous-body data; and
   (c) a step of analyzing microstructure of the porous body by deriving, based on information regarding the placed virtual curved surface solids, an equivalent diameter which is a diameter resulting when the virtual curved surface solid is converted to a sphere and a volume of the virtual curved surface solid, for each of the virtual curved surface solids, deriving an average flow rate of the fluid passing through the virtual curved surface solid for each of the virtual curved surface solids based on both the information regarding the placed virtual curved surface solids and the information regarding the flow rate for each of the space voxels, and deriving a flow-rate-weighted mean diameter that is a weighted average obtained by weighting the equivalent diameter for each of the virtual curved surface solids using a value based on the volume and the average flow rate for each of the virtual curved surface solids.

2. The microstructure analysis method according to claim 1, wherein in the step (c), the flow-rate-weighted mean diameter is derived from the following formula (1):

[Math. 1]

$$Ru = \frac{\sum_{i=1}^{n}(R'_i \times V_i \times U_i)}{\sum_{i=1}^{n}(V_i \times U_i)} \quad \text{formula (1)}$$

Where,
Ru : flow-rate-weighted mean diameter
n : number of virtual curved surface solids that have been placed $R'_i$ equivalent diameter of each virtual curved surface solid (i = 1, 2, ..., n)
$V_i$ : volume of each virtual curved surface solid (i = 1, 2, ..., n)
$U_i$ : average flow gyrate of fluid passing through each virtual curved surface solid (i = 1, 2, ..., n).

3. The microstructure analysis method according to claim 1, wherein in the step (c), the microstructure of the porous body is analyzed by deriving an average value of the equivalent diameters of the plurality of virtual curved surface solids or obtaining an average pore diameter of the porous body to be set as an arithmetic mean diameter, and by deriving a difference between the arithmetic mean diameter and the flow-rate-weighted mean diameter.

4. The microstructure analysis method according to claim 1, wherein in the step (a), a curved surface solid including a parent virtual sphere and one or more child virtual spheres with which voxels occupied by the parent virtual sphere partially overlap is taken as the virtual curved surface solid, and placing the plurality of virtual curved surface solids.

5. The microstructure analysis method according to claim 1, wherein in the step (a), the virtual curved surface solid having the larger equivalent diameter is preferentially placed.

6. A non-transitory computer readable memory storing a program comprising a microstructure analysis method of a porous body using porous-body data in which positional information indicating position of a voxel obtained by three-dimensionally scanning the porous body is associated with voxel-type information indicating whether the voxel is a space voxel representing space or a matter voxel representing object, the method comprising the steps of:
   (a) a step of taking a curved surface solid formed by one virtual sphere or a combination of a plurality of virtual spheres as a virtual curved surface solid, and placing the plurality of virtual curved surface solids so as to fill in the space voxels with curved surface solid voxels which are voxels occupied by the virtual curved surface solid, referring to the porous-body data;
   (b) a step of deriving information regarding a flow rate for each of the space voxels when a fluid passes through the porous body by executing a fluid analysis based on the porous-body data; and
   (c) a step of analyzing microstructure of the porous body by deriving, based on information regarding the placed virtual curved surface solids, an equivalent diameter which is a diameter resulting when the virtual curved surface solid is converted to a sphere and a volume of the virtual curved surface solid, for each of the virtual curved surface solids, deriving an average flow rate of the fluid passing through the virtual curved surface solid for each of the virtual curved surface solids based on both the information regarding the placed virtual curved surface solids and the information regarding the flow rate for each of the space voxels and deriving a flow-rate-weighted mean diameter that is a weighted average obtained by weighting the equivalent diameter for each of the virtual curved surface solids using a value based on the volume and the average flow rate for each of the virtual curved surface solids.

7. A microstructure analysis apparatus comprising:
   storage device that stores porous-body data in which positional information indicating position of a voxel obtained by three-dimensionally scanning the porous body is associated with voxel-type information indicating whether the voxel is a space voxel representing space or a matter voxel representing object, virtual curved surface solid placement device that takes a curved surface solid formed by one virtual sphere or a combination of a plurality of virtual spheres as a virtual curved surface solid, and places the plurality of virtual curved surface solids so as to fill in the space voxels with curved surface solid voxels which are voxels occupied by the virtual curved surface solid, referring to the porous-body data, fluid analysis device that derives information regarding a flow rate for each of the space voxels when a fluid passes through the porous body by executing a fluid analysis based on the porous-body data; and microstructure analysis device that analyzes microstructure of the porous body by deriving, based on information regarding the placed virtual curved surface solids, an equivalent diameter which is a diameter resulting when the virtual curved surface solid is converted to a sphere and a volume of the virtual curved surface solid, for each of the virtual curved surface solids, deriving an average flow rate of the fluid passing through the virtual curved surface solid for each of the virtual curved surface solids based on both the information regarding the placed virtual curved surface solids and the information regarding the flow rate for each of the space voxels, and deriving a flow-rate-weighted mean diameter that is a weighted average obtained by weighting the equivalent diameter for each of the virtual curved surface solids using a value based on the volume and the average flow rate for each of the virtual curved surface solids.

* * * * *